US006943225B2

(12) United States Patent
Lee et al.

(10) Patent No.: US 6,943,225 B2
(45) Date of Patent: Sep. 13, 2005

(54) MULTINUCLEAR METALLOCENE CATALYST

(75) Inventors: Min-Hyung Lee, Tongyoung (KR); Sung-Jin Park, Seoul (KR); Seong-Kyun Kim, Incheon (KR); Young-Jo Kim, Daejeon (KR); Yong-Gyu Han, Daejeon (KR); Young-Kyu Do, Chungchongnam-do (KR); Ki-Ho Choi, Daejeon (KR); Seung-Woong Yoon, Daejeon (KR); Bo-Geun Song, Daejeon (KR); Han-Seock Cho, Daejeon (KR)

(73) Assignee: Honam Petrochemical Corporation (KR)

( * ) Notice: Subject to any disclaimer, the term of this patent is extended or adjusted under 35 U.S.C. 154(b) by 0 days.

(21) Appl. No.: 10/470,346

(22) PCT Filed: Jan. 28, 2002

(86) PCT No.: PCT/KR02/00121

§ 371 (c)(1),
(2), (4) Date: Jul. 29, 2003

(87) PCT Pub. No.: WO02/060964

PCT Pub. Date: Aug. 8, 2002

(65) Prior Publication Data

US 2004/0072677 A1 Apr. 15, 2004

(30) Foreign Application Priority Data

Jan. 29, 2001 (KR) .......................................... 2001-4029

(51) Int. Cl.⁷ ............................... C08F 4/06; C08F 4/72
(52) U.S. Cl. ...................... 526/113; 526/114; 526/116; 526/115; 526/117; 526/160; 526/170; 526/129; 526/130; 526/134; 526/943; 502/103; 502/117
(58) Field of Search ................................. 526/113, 116

(56) References Cited

U.S. PATENT DOCUMENTS

| 5,372,980 A | | 12/1994 | Davis ......................... 502/103 |
| 5,439,994 A | * | 8/1995 | Inoue et al. ................. 526/114 |
| 5,830,958 A | | 11/1998 | Peifer et al. ................. 526/113 |
| 6,010,974 A | | 1/2000 | Kim et al. ................... 502/152 |
| 6,114,556 A | | 9/2000 | Aulbach et al. .............. 556/11 |
| 6,153,776 A | * | 11/2000 | Patton et al. ................. 556/11 |
| 6,288,254 B1 | | 9/2001 | Chen et al. ................... 556/11 |

FOREIGN PATENT DOCUMENTS

EP          0985676          3/2000         ........... C07F/17/00

OTHER PUBLICATIONS

Liu et al. (Huaxue Xuebao, 1993, 51(11), 1118–1124 (Abstract only).*
Deng et al. (Gaodeng Xuexiao Hauxue Xuebao, 2002, 23(11), 2089–2092 (Abstract only).*
Tian et al. (Chinese Journal of Polymer Science, 1998, 16(4), 370–376 (Abstract only).*
Jungling, S.; Mulhaput, R.; Plenio, H. J. Orgnomet. Chem. 1993, 460, 191–195.*

* cited by examiner

Primary Examiner—David W. Wu
Assistant Examiner—Rip A. Lee
(74) Attorney, Agent, or Firm—Dilworth & Barrese, LLP

(57) ABSTRACT

The present invention relates to a multinuclear metallocene catalyst for olefin polymerization and a process for olefin polymerization using the same, in which the multinuclear metallocene catalyst for olefin polymerization comprises, as a main catalyst, a transition metal compound that contains at least two metal atoms in the groups III to X of the periodic table as central metals and a ligand having a cyclopentadienyl structure bridging between the two metal atoms, and, as a cocatalyst, an aluminoxane compound, an organoaluminum compound or a bulky compound reactive to the transition metal compound to impart a catalytic activity to the transition metal compound.

20 Claims, 3 Drawing Sheets

MULTINUCLEAR METALLOCENE CATALYST

TECHNICAL FIELD

The present invention relates to a multinuclear metallocene catalyst for olefin polymerization containing at least two active sites and a high polymerization activity, and a process for olefin polymerization using the same. More particularly, the present invention relates to a multinuclear metallocene catalyst for olefin polymerization and a process for olefin polymerization using the same, in which the multinuclear metallocene catalyst for olefin polymerization comprises as a main catalyst a transition metal compound containing at least two metal atoms in the groups III to X of the periodic table as central metals and a ligand having a cyclopentadienyl structure bridging between the two metal atoms, and as a cocatalyst an aluminoxane compound, an organoaluminum compound or a bulky compound reactive to the transition metal compound to impart a catalytic activity to the transition metal compound.

BACKGROUND ART

Since the Ziegler-Natta catalyst was developed in the middle of the 1950's, polyethylene, isotactic polypropylene and ethylene propylene diene copolymers (EPDM) of different properties have been produced. The Ziegler-Natta catalyst, of which the active sites are not uniform, is inapplicable to the preparation of polymers of narrow molecular weight distribution MwD and compositional distribution.

An appearance of a metallocene catalyst in the middle of the 1980's enabled to produce polymers of various properties that are otherwise impossible to produce with the Ziegler-Natta catalyst, as well as polymers of narrow molecular weight distribution and compositional distribution. In particular, the polymers of narrow molecular weight distribution and compositional distribution that are polymerized using the metallocene catalyst have a high strength relative to the polymers of broad molecular distribution and compositional distribution polymerized in the presence of the Ziegler-Natta catalyst, and reduce the stickiness in the manufacture of films or sheets. However, those polymers require an extremely high energy in processing because of its narrow molecular weight distribution.

Accordingly, many studies have been made in many countries of the world on the multinuclear metallocene catalysts for the sake of overcoming the drawbacks of the polymers of narrow molecular weight distribution. Examples of the related art can be described as follows.

First, U.S. Pat. No. 5,525,678 (Jun. 11, 1996) discloses a binuclear catalyst system for olefin polymerization that comprises a metallocene compound and a non-metallocene compound supported on a support, making it possible to, produce a high molecular weight polymer and a low molecular weight polymer at once. But, the catalyst system requires complex processes in regard to independent supporting of the metallocene compound and the non-metallocene compound and pretreatment of the support with different compounds for the supporting reaction.

U.S. Pat. No. 5,700,886 (Dec. 23, 1997) describes a polymerization method using at least two metallocene compounds as catalysts in a single reactor to control the molecular weight distribution of the polymer. This method is problematic in that a high expense for catalysts and strict polymerization conditions are required in the polymerization reaction to produce polymers of a desired molecular weight distribution because of using two or more metallocene compounds of a complicated structure.

Alternatively, U.S. Pat. No. 5,753,577 (May 19, 1998) discloses a binuclear metallocene compound containing two metal atoms in the group IV of the periodic table as central metals, which have an oxidation number of +3 and are linked together by a direct chemical bond, the metallocene compound also having a chemical bond bridging between ligands bonded to the central metals. The use of the catalyst for polymerization, however, results in polymers having a low molecular weight.

U.S. Pat. No. 5,442,020 (Aug. 15, 1995) discloses an ethylene, propylene or ethylene-alpha-olefin polymerization method using a binuclear metallocene compound that is prepared by reacting a group IV metal compound with an alkylene/silylene-bridged cyclopentadienyl group. But, the preparation of the catalyst requires a complex process in regard to introduction of alkylene or silylene groups to the catalyst.

U.S. Pat. No. 5,627,117 (May 6, 1997) describes an ethylene, propylene or ethylene-alpha-olefin polymerization method using a multinuclear metallocene compound that is prepared by reacting a group IV to VIII metal compound with a cyclopentadienyl group linked to alkylene or silylene groups or divalent germanium (Ge) or tin (Sn). But, the catalyst has a low activity for high-temperature polymerization relative to the existing catalysts.

In addition, U.S. Pat. No. 6,010,974 (Jan. 4, 2000) discloses a styrene polymerization method using a binuclear metallocene compound that is prepared by reacting a group IV metal compound with an alkylene/silylene-bridged cyclopentadienyl group. The use of this catalyst is however limited to the preparation of styrene polymer or styrene copolymer.

DISCLOSURE OF INVENTION

In an attempt to provide a catalyst for olefin polymerization that has a high polymerization activity and is used to produce polymers of controllable molecular weight and the molecular weight distribution, the inventors of the present invention have found out that the problems with the prior art can be solved by using a catalyst for olefin polymerization that comprises as a main catalyst a transition metal compound containing at least two metal atoms in the groups III to X of the periodic table as central metals and a ligand having a cyclopentadienyl structure bridging between the two metal atoms, and as a cocatalyst an aluminoxane compound, an organoaluminum compound or a bulky compound reactive to the transition metal compound to impart a catalytic activity to the transition metal compound, thereby completing the present invention.

It is therefore an object of the present invention to provide a novel multinuclear organometallic catalyst for olefin polymerization that produces polymers of controllable molecular weight and molecular weight distribution in a homogenous or heterogeneous state and has a high polymerization activity.

It is another object of the present invention to provide a process for olefin polymerization using the catalyst to prepare olefin polymers having different molecular weights and various molecular weight distributions.

To achieve the objects of the present invention, there is provided a multinuclear catalyst for olefin polymerization comprising: (A) a transition metal compound that has at least two metal atoms in the groups III to X of the periodic table as central metals, and a ligand of a cyclopentadienyl structure bridging between the two metal atoms; and (B) an aluminoxane compound, an organoaluminum compound, or a bulky compound reactive to the transition metal compound to impart a catalytic activity to the transition metal compound.

Hereinafter, the present invention will be described in more detail.

The catalyst for olefin polymerization according to the present invention comprises (A), as a main catalyst, a transition metal compound that contains at least two metal atoms in the groups III to X of the periodic table as central metals and a ligand of a cyclopentadienyl structure bridging between the two metal atoms; and (B), as a cocatalyst, an aluminoxane compound, an organoaluminum compound, or a bulky compound reactive to the transition metal compound to impart a catalytic activity to the transition metal compound.

In the catalyst for olefin polymerization according to the present invention, the transition metal compound (A) as a main catalyst contains at least two metal atoms in the groups III to X of the periodic table as central metals and a ligand of a cyclopentadienyl structure bridging between the two metal atoms, the transition metal compound being represented by the formula 1:

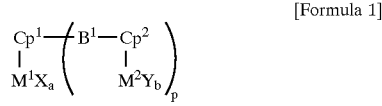

[Formula 1]

wherein $M^1$ and $M^2$ are the same or different and each represents an element in the groups III to X of the periodic table; $Cp^1$ and $Cp^2$ are the same or different and each represents a ligand of an unsubstituted or substituted cyclopentadienyl structure, the substituted cyclopentadienyl structure having at least one substituent selected from the group consisting of a $C_1$–$C_{20}$ alkyl group, a $C_3$–$C_{20}$ cycloalkyl group, a $C_1$–$C_{20}$ alkylsilyl group, a $C_1$–$C_{20}$ haloalkyl group, a $C_6$–$C_{20}$ aryl group, a $C_6$–$C_{20}$ arylalkyl group, a $C_6$–$C_{20}$ arylsilyl group, a $C_6$–$C_{20}$ alkylaryl group, a $C_1$–$C_{20}$ alkoxy group, a $C_1$–$C_{20}$ alkylsiloxy group, a $C_6$–$C_{20}$ aryloxy group, a halogen atom and an amino group; and $B^1$ represents a $C_5$–$C_{40}$ arylene group or an arylene group represented by the formula 2:

[Formula 2]

wherein Ary represents a $C_6$–$C_{20}$ arylene group directly bonded to $Cp^1$ and $Cp^2$; $B^{1'}$ represents a $C_1$–$C_{20}$ alkylene group, a $C_3$–$C_{20}$ cycloalkylene group, a $C_1$–$C_{20}$ alkylsilylene group, a $C_1$–$C_{20}$ haloalkylene group, a $C_6$–$C_{20}$ arylalkylene group or a $C_6$–$C_{20}$ arylsilylene group; and q is an integer from 0 to 5;

X and Y are the same or different and each represents $Cp^1$ or $Cp^2$, a $C_1$–$C_{20}$ alkyl group, a $C_3$–$C_{20}$ cycloalkyl group, a $C_1$–$C_{20}$ alkylsilyl group, a $C_1$–$C_{20}$ haloalkyl group, a $C_6$–$C_{20}$ aryl group, a $C_6$–$C_{20}$ arylalkyl group, a $C_6$–$C_{20}$ arylsilyl group, a $C_6$–$C_{20}$ alkylaryl group, a $C_1$–$C_{20}$ alkoxy group, a $C_1$–$C_{20}$ alkylsiloxy group, a $C_6$–$C_{20}$ aryloxy group, a halogen atom, an amino group or a tetrahydroborate group; a and b are an integer from 1 to 5 determined by the oxidation number of the central metal; and p is an integer from 1 to 3.

Preferably, the transition metal compound represented by the formula 1 is a transition metal compound represented by the formula 3, where p is 1:

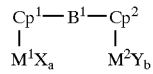

[Formula 3]

wherein $M^1$, $M^2$, $Cp^1$, $Cp^2$, $B^1$, X, Y, a and b are the same as defined the formula 1 and p is 1.

In the formula 1 of the transition metal compound used in the present invention, $M^1$ and $M^2$ are preferably an element in the group IV of the periodic table, more preferably zirconium (Zr), titanium (Ti) or hafnium (Hf).

In the formula 1 of the transition metal compound used in the present invention, the ligand of the cyclopentadienyl structure of $Cp^1$ and $Cp^2$ includes, for example, a cyclopentadienyl group, an indenyl group or a fluorenyl group. The substituent of the ligand of the cyclopentadienyl structure includes, for example, $C_1$–$C_{20}$ alkyl groups such as methyl, ethyl, propyl, butyl, pentyl and hexyl; $C_3$–$C_{20}$ cycloalkyl groups such as cyclopropyl, cyclobutyl, cyclopentyl and cyclohexyl; $C_1$–$C_{20}$ alkylsilyl groups such as methylsilyl, dimethylsilyl, trimethylsilyl, ethylsilyl, diethylsilyl, trietlhylsilyl, propylsilyl, dipropylsilyl, tripropylsilyl, butylsilyl, dibutylsilyl and tributylsilyl; $C_1$–$C_{20}$ haloalkyl groups such as trifluoromethyl; $C_6$–$C_{20}$ aryl groups such as phenyl, biphenyl, terphenyl, naphthyl, fluorenyl and benzyl; $C_6$–$C_{20}$ arylalkyl groups such as phenylethyl and phenylpropyl; $C_6$–$C_{20}$ arylsilyl groups such as phenylsilyl, phenyldimethylsilyl, diphenylmethylsilyl and triphenylsilyl; $C_6$–$C_{20}$ alkylaryl groups such as methylphenyl, dimethylphenyl, trimethylphenyl, ethylphenyl, diethylphenyl, triethylphenyl, propylphenyl, dipropylphenyl and tripropylphenyl; $C_1$–$C_{20}$ alkoxy groups such as methoxy, ethoxy, propoxy, butoxy, pentoxy and hexyloxy; $C_1$–$C_{20}$ alkylsiloxy groups such as methylsiloxy, dimethylsiloxy, trimethylsiloxy, ethylsiloxy, diethylsiloxy and triethylsiloxy; $C_6$–$C_{20}$ aryloxy groups such as phenoxy, naphthoxy, methylphenoxy, dimethylphenoxy, trimethylphenoxy, ethylphenoxy, diethylphenoxy, triethylphenoxy, propylphenoxy, dipropylphenoxy and tripropylphenoxy; halogen atoms; or amino groups such as a dimethylamono group, a diethylamino group, a dipropylamino group, a dibutylamino group, a diphenylamino group and a dibenzylamino group. In the case where the cyclopentadienyl structure has at least two substituents, the substituents may be bonded together to form a ring compound.

In the formula 1 of the transition metal compound used in the present invention, $Cp^1$ and $Cp^2$ are preferably cyclopentadienyl, methylcyclopentadienyl, dimethylcyclopentadienyl, trimethylcyclopentadienyl, tetramethylcyclopentadienyl, ethylcyclopentadienyl, diethylcyclopentadienyl, triethylcyclopentadienyl, n-propylcyclopentadienyl, iso-propylcyclopentadienyl, n-butylcyclopentadienyl, iso-butylcyclopentadienyl, tert-butylcyclopentadienyl, indenyl, methylindenyl, dimethylindenyl, trimethylindenyl, ethylindenyl, diethylindenyl, or thiethylindenyl.

In the formula I-1 of the transition metal compound used in the present invention, $B^1$ is a divalent hydrocarbyl radical bridging between $Cp^1$ and $Cp^2$. Examples of the arylene group as $B^1$ include phenylene, biphenylene, terphenylene, naphthylene, binaphthylene, fluorenylene, anthracylene, pyridylene, bipyridylene, terpyridylene, quinolylene, pyridazylene, pyrimidylene, pyrazylene, or quinoxalylene. Examples of $B^{1'}$ include methylene, dimethylmethylene, diethylmethylene, diphenylmethylene, ethylene, methylethylene, dimethylethylene, trimethylethylene, tetramethylethylene, tetraethylethylene, tetraphenylethylene, propylene, butylene, dimethylsilylene, diethylsilylene, diphenylsilylene, cyclohexylene, or tetrafluoroethylene.

In the formula 1 of the transition metal compound used in the present invention, $B^1$ is preferably phenylene, biphenylene, methylene-4,4'-biphenylene, 1,2-ethylene-4,4'-biphenylene, 1,3-propylene-4,4'-biphenylene, 1,4-butylene-4,4'-biphenylene, terphenylene, anthracylene, or pyridylene.

In the formula 1 of the transition metal compound used in the present invention, X or Y preferably includes $Cp^1$ or $Cp^2$, $C_6$–$C_{20}$ aryloxy groups, or halogen atoms. More preferably, at least one of X and Y is cyclopentadienyl, methylcyclopentadienyl, dimethylcyclopentadienyl, trimethylcyclopentadienyl, tetramethylcyclopentadienyl, pentamethylcyclopentadienyl, ethylcyclopentadienyl, diethylcyclopentadienyl, triethylcyclopentadienyl, n-propylcyclopentadienyl, iso-propylcyclopentadienyl, n-butylcyclopentadienyl, iso-butylcyclopentadienyl, tert-butylcyclopentadienyl, indenyl, methylindenyl, dimethylindenyl, trimethylindenyl, ethylindenyl, diethylindenyl, triethylindenyl, phenoxy, naphthoxy, methylphenoxy, dimethylphenoxy, trimethylphenoxy, ethylphenoxy, diethylphenoxy, triethylphenoxy, propylphenoxy, dipropylphenoxy, tripropylphenoxy, fluorine, chlorine, bromine, or iodine. The number of halogen atoms bonded to the central metal depends on the oxidation state of the central metal.

When p is 1 in the formula 1, the transition metal compound is a $B^1$-bridged binuclear transition metal compound as represented by the formula I-2; and when p is 2, the transition metal compound is a ternuclear transition metal compound in which one more $B^1$ is linked to $Cp^2$.

The preparation of the transition metal compound (A) represented by the formula 1 may include, if not specifically limited to, reacting all the compounds of the following formulas 4, 5 and 6 at once, or reacting the compound of the formula 4 with that of the formula 5 and then adding the compound of the formula 6 to the resulting reactant, in which the compound of the formula 5 may be the same as that of the formula 6:

   [Formula 4]

wherein $Cp^1$, $Cp^2$, $B^1$ and p are as defined above in the formula 1; $M^3$ is an alkali metal such as lithium (Li), sodium (Na) and potassium (K), aluminum (Al), or thallium (Tl); and r is an integer from 1 to 4;

H-MX,   [Formula 5]

wherein H is a halogen atom; and $M^1$, X and a are as defined above in the formula 1; and H-$M^2Y_b$   [Formula 6]

wherein H is a halogen atom; and $M^2$, Y and b are as defined above in the formula 1.

Alternatively, the transition metal compound (A) represented by the formula 3 may be prepared by reacting the compounds of the following formulas 7 and 8:

   [Formula 7]

wherein $Cp^1$, $M^1$, X and a are as defined above in the formula 3; and $B^{11}$ is a substituent capable of forming $B^1$ in the reaction; and

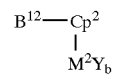   [Formula 8]

wherein $Cp^2$, $M^2$, Y and b are as defined above in the formula 3; and $B^{12}$ is a substituent capable of forming $B^1$ in the reaction.

In the polymerization catalyst of the present invention, the aluminoxane compound, the organoaluminum compound or bulky compound reactive to the transition metal compound to impart the catalytic activity to the transition metal compound used as a cocatalyst. The aluminoxane compound (B) is represented by the following formula 9 and has a linear, annular or network structure. Specific examples of the aluminoxane compound include methylaluminoxane, ethylaluminoxane, butylaluminoxane, hexylaluminoxane, octylaluminoxane and decylaluminoxane.

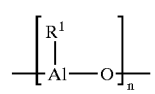   [Formula 9]

wherein $R^1$ represents a $C_1$–$C_{10}$ alkyl group; and n is an integer from 1 to 70.

In the polymerization catalyst of the present invention, the organoaluminum compound (B) used as a cocatalyst is represented by the following formula 10 and includes, for example, trialkylaluminum such as trimethylaluminum, triethylaluminum, tributylaluminum, trihexylaluminum, trioctylaluminum and tridecylaluminum; dialkylaluminum alkoxide such as dimethylaluminum methoxide, diethylaluminum methoxide and dibutylaluminum methoxide; dialkylaluminum halide such as dimethylaluminum chloride, diethylaluminum chloride and dibutylaluminum chloride; alkylaluminum dialkoxide such as methylaluminum dimethoxide, ethylaluminum dimethoxide and butylaluminum dimethoxide; or alkylaluminum dihalide such as methylaluminum dichloride, ethylaluminum dichloride and butylaluminum dichloride.

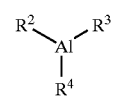   [Formula 10]

wherein $R^2$, $R^3$ and $R^4$ are the same or different and each represents a $C_1$–$C_{10}$ alkyl group, a $C_1$–$C_{10}$ alkoxy group or a halide group, at least one of $R^2$, $R^3$ and $R^4$ including an alkyl group.

In the polymerization catalyst of the present invention, the bulky compound (B) reactive to the transition metal compound to impart a catalytic activity to the transition metal compound is represented by the following formula 11 and includes, for example, trimethylammonium tetraphenylborate, triethylammonium tetraphenylborate, tripropylammonium tetraphenylborate, tributylammonium tetraphenylborate, trimethylammonium tetrakis(pentafluorophenyl)borate, triethylammonium tetrakis(pentafluorophenyl)borate, tripropylammonium tetrakis(pentafluorophenyl)borate, tributylammonium tetrakis(pentafluorophenyl)borate, anilium tetraphenylborate, anilium tetrakis(pentafluorophenyl)borate, pyridinium tetraphenylborate, pyridinium tetrakis(pentafluorophenyl)borate, ferrocenium tetrakis(pentafluorophenyl)borate, silver tetraphenylborate, silver tetrakis(pentafluorophenyl)borate, tris(pentafluorophenyl)borane, tris(2,3,5,6-tetrafluorophenyl)borane or tris(3,4,5-triflurorophenyl)borane.

[C][D]  [Formula 11]

wherein C represents the proton-bonded cation of a Lewis base, or an oxidative metallic or non-metallic compound; and D is a compound of an element in the groups V to XV of the periodic table and an organic substance.

The cocatalyst of the polymerization catalyst of the present invention, that is, the aluminoxane compound, the organoaluminum compound or the bulky compound reactive to the transition metal compound to impart a catalytic activity to the transition metal compound is not limited to the above examples and may be used alone or in combination in the olefin polymerization.

On the other hand, the polymerization catalyst of the present invention may be supported on a support such as an organic or inorganic compound and used as a supported catalyst. To support the catalyst on the support, there may be used various methods, which may include supporting the main catalyst (A) directly on a dehydrated support; pretreating the support with the cocatalyst (B) and then supporting the main catalyst (A) on the support; supporting the main catalyst (A) on the support and then adding the cocatalyst (B); or reacting the main catalyst (A) with the cocatalyst (B) and then with the support.

The support used for the polymerization catalyst of the present invention is not specifically limited and may be any inorganic compound that has fine pores on the surface and a large surface area. Examples of the inorganic compound used as the support may include silica, alumina, bauxite, zeolite, $MgCl_2$, $CaCl_2$, MgO, $ZrO_2$, $TiO_2$, $B_2O_3$, CaO, ZnO, $BaO$, $ThO_2$, or a mixture thereof, for example, $SiO_2$—MgO, $SiO_2$—$Al_2O_3$, $SiO_2$—$TiO_2$, $SiO_2$—$V_2O_5$, $SiO_2$—$CrO_2O_3$ or $SiO_2$—$TiO_2$—MgO. These compounds may contain a small amount of carbonate, sulfate or nitrate. Examples of the organic compound used as the support may include starch, cyclodextrine, or synthetic polymer.

Examples of the solvent used in supporting the polymerization catalyst of the present invention may include aliphatic hydrocarbons such as pentane, hexane, heptane, octane, nonane, decane, undecane and docecane; aromatic hydrocarbons such as benzene, mono-chlorobenzene, dichlorobenzene, trichlorobenzene and toluene; or halogenated aliphatic hydrocarbons such as dichloromethane, trichloromethane, dichloroethane and trichloroethane. These solvents are used alone or in combination during the supporting method.

Though the amounts of the transition metal compound (A) and the aluminoxane compound (B), the organoaluminum compound (B) or the bulky compound (B) reactive to the transition metal compound to impart a catalytic activity to the transition metal compound used in supporting the polymerization catalyst of the present invention are not specifically limited, the mole ratio of (B) to (A) is preferably 1 to $10^4:1$, more preferably 1 to $5 \times 10^2:1$.

The temperature for supporting the polymerization catalyst of the present invention is preferably 0 to 120° C., more preferably 20 to 100° C.

The polymerization reaction using the polymerization catalyst of the present invention may be performed in a slurry, liquid, gas or bulk state. In the case of polymerization in the liquid or slurry state, the solvent or olefin itself may be used as the medium and the olefin for the polymerization reaction may be used alone or in combination of at least two types. Examples of the solvent used in the polymerization reaction may include butane, pentane, hexane, octane, decane, dodecane, cyclopentane, methylcyclopentane, cyclohexane, benzene, toluene, xylene, dichloromethane, chloroethane, 1,2-dichloroethane and chlorobenzene. These solvents may be used in combination at a predetermined mixing ratio.

Examples of the olefin used in the olefin polymerization of the present invention may include $C_2$–$C_{20}$ α-olefin such as ethylene, propylene, 1-butene, 1-pentene and 1-hexene; $C_4$–$C_{20}$ diolefin such as 1,3-butadiene, 1,4-pentadiene and 2-methyl-1,3-butadiene; $C_3$–$C_{20}$ cycloolefin or diolefin such as cyclopentene, cyclohexene, cyclopentadiene, cyclohexadiene, norbonene and methyl-2-norbonene; or unsubstituted or substituted styrene, the substituted styrene having a substituent such as an alkyl group, a $C_1$–$C_{10}$ alkoxy group, a halogen group, an amine group, a silyl group or a halogenated alkyl group. These olefins may be used alone or in combination in the polymerization reaction.

Though the amount of the transition metal compound (A) for olefin polymerization using the polymerization catalyst of the present invention is not specifically limited, the concentration of the central metal in the polymerization reaction system is preferably $10^{-8}$ to $10^1$ mol/l, more preferably $10^{-7}$ to $10^{-2}$ mol/l.

Though the amount of the aluminoxane compound (B), the organoaluminum compound (B) or the bulky compound (B) reactive to the transition metal compound to impart a catalytic activity to the transition metal compound used for the olefin polymerization of the present invention is not specifically limited, the mole ratio of (B) to (A) is preferably 1 to $10^6:1$, more preferably 1 to $5 \times 10^4:1$.

The temperature for the olefin polymerization of the present invention is not specifically limited and may be –50 to 200° C., preferably 0 to 150° C. The olefin polymerization may be performed in a batch, semi-continuous or continuous system under the polymerization pressure of 1.0 to 3,000 atmospheres, preferably 2 to 1,000 atmospheres.

BEST MODE FOR CARRYING OUT THE INVENTION

Figure 1:
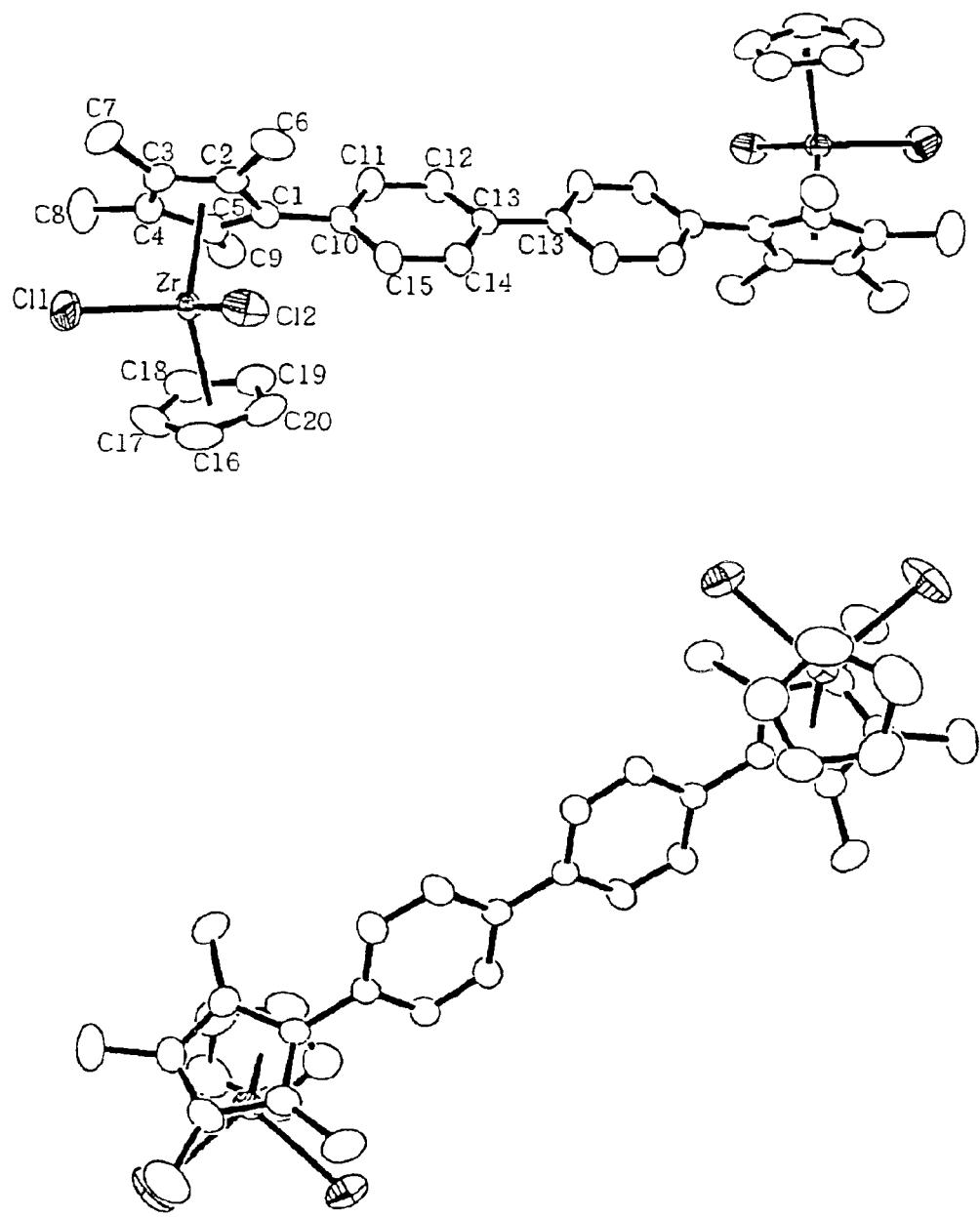
FIG. 1 shows an X-ray molecular structure of the compound prepared in Synthesis Example 1 of the present invention.

Hereinafter, the present invention will be described in further detail by way of the following synthetic examples and polymerization examples, which are not intended to limit the scope of the present invention.

SYNTHESIS EXAMPLES

Synthesis of Transition Metal Compound (A)

All the syntheses were performed in the inert (e.g., nitrogen or argon) atmosphere using the standard Schlenk method and the glove box method.

For purification, there were used sodium-potassium alloy for tetrahydrofuran (THF), toluene and n-hexane, sodium-benzophenone ketyl for diethylether, or calcium hydride ($CaH_2$) for methylene chloride ($CH_2Cl_2$). Deuterium-substituted chloroform ($CDCl_3$) used in the analysis of the organometallic compounds was dried on an activated molecular sieve 4A.

Some compounds commercially available were used without any further purification, examples of which may include 4,4'-dibromobiphenyl, 1,4-dibromobenzene, 4-bromobenzyl bromide, 2,3,4,5-tetramethyl-2-cyclopentenone, 2,6-diisopropylphenol, n-butyllithium (2.5M solution in n-Hexane), phenylmagnesium chloride (2.0M solution in THF), para-toluenesulfonic acid monohydrate (p-TsOH.$H_2O$), trimethylsilyl chloride ($Me_3SiCl$; TMSCl), triisopropoxytitanium chloride ($ClTi(OiPr)_3$), cyclopentadienylzirconium trichloride ($CpZrCl_3$) and pentamethylcyclopentadienyltitanium trichloride ($Cp.TiCl_3$).

$^1H$ NMR and $^{13}C$ NMR were measured with a Bruker Avance 400 spectrometer, and the element analysis was performed with an EA 1110-FISION (CE Instruments). The X-ray molecular structure was analyzed with an Enrarf-Nonius CAD4TSB diffractometer and interpreted through computations on a Silicon Graphics Indigo2XZ workstation.

Synthesis Example 1

4,4'-biphenylene bis(2,3,4,5-tetramethylcyclopentadienyl) di (cyclopentanedienylzirconium dichloride) ([4,4'-$(C_5Me_4)_2(C_6H_4)_2$][$CpZrCl_2$]$_2$)

Synthesis Example 1—1

4,4'-bis(2,3,4,5-tetramethylcyclopentadienyl) biphenylene (4,4'-$(C_5Me_4H)_2(C_6H_4)_2$)

9.36 g (30 mmol) of 4,4'-dibromobiphenyl was mixed with 40 ml of diethylether to obtain a slurry and 24 ml (2 equivalent weights) of n-butyllithium was added to the slurry at −30° C. The temperature was then raised to 0° C. to turn the reaction solution clear and produce a precipitate (4,4'-biphenyl dilithium salt). At this temperature, the reaction solution was stirred for more 30 minutes, warmed to the room temperature and further stirred until the precipitate does not form any more. After malting the precipitate settle and discarding the supernatant, 30 ml of tetrahydrofuran was added and the reaction solution was cooled to −78° C. To the reaction solution was slowly added a solution prepared by dissolving 8.29 g of 2,3,4,5-tetramethyl-2-cyclopentenone in 20 ml of tetrahydrofuran. The reaction solution was then warmed to the room temperature and stirred overnight, and 30 ml of a saturated ammonium chloride ($NH_4Cl$) solution was added to terminate the reaction.

The organic layer was separated from the aqueous layer. The product was more extracted from the aqueous layer with 50 ml of diethylether and the diethylether layer was combined with the previously separated organic layer. The combined organic layer was removed of the surplus water on anhydrous magnesium sulfate ($MgSO_4$). The solid was filtered out and a colorless oily product was obtained after evaporation of the solvent.

The product thus obtained was not purified but dissolved in 30 ml of methylene chloride at the room temperature. 0.1 g of p-toluenesulfonate hydrate in the solid state was added to immediately obtain an ivory solid product. After stirred for more 30 minutes, the solid product was subjected to vacuum until a small amount of methylene chloride remains as to wet the solid product. 30 ml of n-hexane was added in order to further precipitate the solid product and dissolve the non-reacted substances. The ivory yellow solid product thus obtained was isolated with a glass filter, washed with each 30 ml of ethanol, diethylether and n-pentane in order and dried under vacuum to produce 7.50 g (63% yield) of the title compound.

$^1H$ NMR (400.13 MHz, $CDCl_3$): d 7.61 (d, 4H), 7.30 (d, 4H), 3.22 (q, 2H), 2.08 (s, 6H), 1.94 (s, 6H), 1.87 (s, 6H), 0.99 (s, 6H). $^{13}C\{^1H\}$ NMR (100.62 MHz, $CDCl_3$): d 142.3, 140.9, 137.8, 137.5, 135.8, 135.2, 128.7, 126.5, 50.0, 14.9, 12.9, 12.0, 11.1.

The synthesis process is presented in the following scheme 1.

Synthesis Example 1-2

4,4'-biphenylene bis(2,3,4,5-tetramethylcyclopentadienyl) di (Cyclopentanedienylzirconium dichloride) ([4,4'-$(C_5Me_4)_2(C_6H_4)_2$][$CpZrCl_2$]$_2$)

0.592 g of 4,4'-bis(2,3,4,5-tetramethylcyclopentadienyl) biphenylene prepared in Synthesis Example 1—1 was dissolved in 20 ml of tetrahydrofuran. 1.2 ml (2 equivalent weights) of n-butyllithium was then added to the reaction solution. The temperature was raised to the room temperature with stirring overnight to obtain a brown solid product in the green-purple solution. The reaction solution was cooled down to −78° C. and 0.788 g (2 equivalent weights, 3.0 mmol) of cyclopentadienylzirconium trichloride ($CpZrCl_3$) slurry in 10 ml of tetrahydrofuran was added to the reaction solution. The reaction solution was warmed to the room temperature and stirred for more one hour to obtain a yellow solution, which was refluxed overnight with stirring. The light orange solution thus obtained was dried under vacuum and 30 ml of methylene chloride was added to the solution to dissolve the product.

The methylene chloride solution was filtered out through a celite layer to obtain a yellowish green solution and methylene chloride was vaporized to obtain a solid product, which was washed with 10 ml of n-hexane/diethylether (v/v=2/1) twice and dried under vacuum to produce 1.02 g (80% yield) the light yellowish title compound.

$^1H$ NMR (400.13 MHz, $CDCl_3$): 7.69 (d, 4H), 7.25 (d, 4H), 6.17 (s, 10H), 2.27 (s, 12H), 2.07 (s, 12H). $^{13}C\{^1H\}$ NMR (100.62 MHz, $CDCl_3$): 138.9, 133.3, 130.3, 126.8, 126.6, 126.2, 123.7, 116.7, 14.0, 12.3.

Anal. Calcd for $C_{40}H_{42}Cl_4Zr_2$: C, 56.72; H, 5.00. Found: C, 56.96; H, 5.89.

The synthesis process is presented in the following scheme 1, and the X-ray molecular structure of 4,4'-biphenylene bis(2,3,4,5-tetramethylcyclopentadienyl) di(cyclopentanedienylzirconium dichloride) is shown in FIG. 1.

[Scheme1]

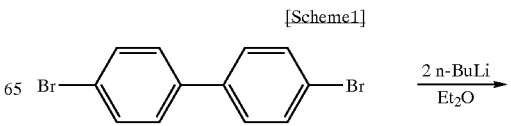

-continued

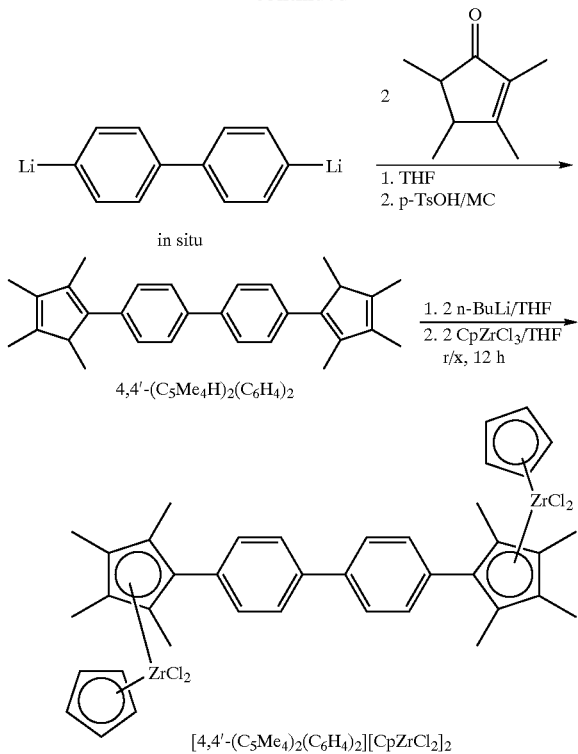

4,4'-(C5Me4H)2(C6H4)2

[4,4'-(C5Me4)2(C6H4)2][CpZrCl2]2

Synthesis Example 2

4,4'-biphenylene bis(2,3,4,5-tetramethylcyclopentadienyl) di(titanium trichloride) ([4,4'-(C5Me4)2(C6H4)2][TiCl3]2)

In the same manner as described in Synthesis Example 1-2, 1.97 g (5.0 mmol) of 4,4'-bis(2,3,4,5-tetramethylcyclopentadienyl) biphenylene was reacted with 2 equivalent weights of n-butyllithium. 4,4'-bis(2,3,4,5-tetramethylcyclopentadienyl) biphenylene dilithium salt thus obtained was changed to slurry in 20 ml of tetrahydrofuran and added to 20 ml of a tetrahydrofuran solution containing 2 equivalent weights of triisopropoxytitanium chloride (ClTi(OiPr)3). The reaction solution was warmed to the room temperature and stirred for more 3 hours. After vaporizing tetrahydrofuran off, 30 ml of methylene chloride was added to dissolve the reaction product. The methylene chloride solution was filtered out through a celite layer and the solid byproduct was removed to obtain a light greenish solution. An excess of trimethylsilyl chloride ((CH3)3SiCl, 3 equivalents, 11 ml) was then added to the solution at 0° C. The solution was warmed to the room temperature and stirred to observe that a red precipitate is slowly formed. After stirring the reaction solution overnight, methylene chloride was vaporized to slightly wet the solid product, which was washed with 20 ml of n-hexane/diethylether (v/v=2/1) twice and dried under vacuum to produce 1.20 g (34% yield) of the title compound in scarlet fine crystals.

$^1$H NMR (400.13 MHz, CDCl3): 7.70 (d, 4H), 7.46 (d, 4H), 2.51 (s, 12H), 2.44 (s, 12H).

The synthesis process is presented in the following scheme 2.

Synthesis Example 3

4,4'-biphenylene bis(2,3,4,5-tetramethylcyclopentadienyl) di(2,6-diisopropylphenoxytitanium dichloride) ([4,4'-(C5Me4)2(C5Me4)2(C6H4)2][Ti(O-2,6-iPr2Ph)Cl2]2)

0.351 g (0.5 mmol) of 4,4'-biphenylene bis(2,3,4,5-tetramethylcyclopentadienyl) di(titanium trichloride) prepared in Synthesis Example 2 and 0.184 g (2 equivalent weights) of 2,6-diisopropylphenol lithium salt were added to the same reactor. After adding 20 ml of tetrahydrofuran at −78° C., the reaction solution was slowly warmed to the room temperature and stirred for more 6 hours. Following the vaporization of tetrahydrofuran, the reaction product was extracted with methylene chloride and passed through a celite pad to remove byproducts. Methylene chloride was vaporized to 10 ml. 20 ml of n-hexane was added to the condensed solution to cause phase separation and cooled down to −20° C. to obtain 0.271 g (55% yield) of the title compound in red crystals.

$^1$H NMR (400.13 MHz, CDCl3): 7.66 7.58 (m, 8H), 7.01 6.98 (m, 6H), 3.03 (sept, 4H), 2.33 (s, 12H), 2.28 (s, 12H), 1.04 (d, 24H). $^{13}$C{$^1$H} NMR (100.62 MHz, CDCl3): 159.9, 139.9, 139.6, 136.2, 133.6, 132.3, 131.1, 130.9, 126.8, 123.6, 123.2, 26.8, 23.8, 14.0, 13.3.

Anal. Calcd for $C_{54}H_{66}Cl_4O_2Ti_2$: C, 65.87; H, 6.76. Found: C, 66.14; H, 7.27.

Figure 2:
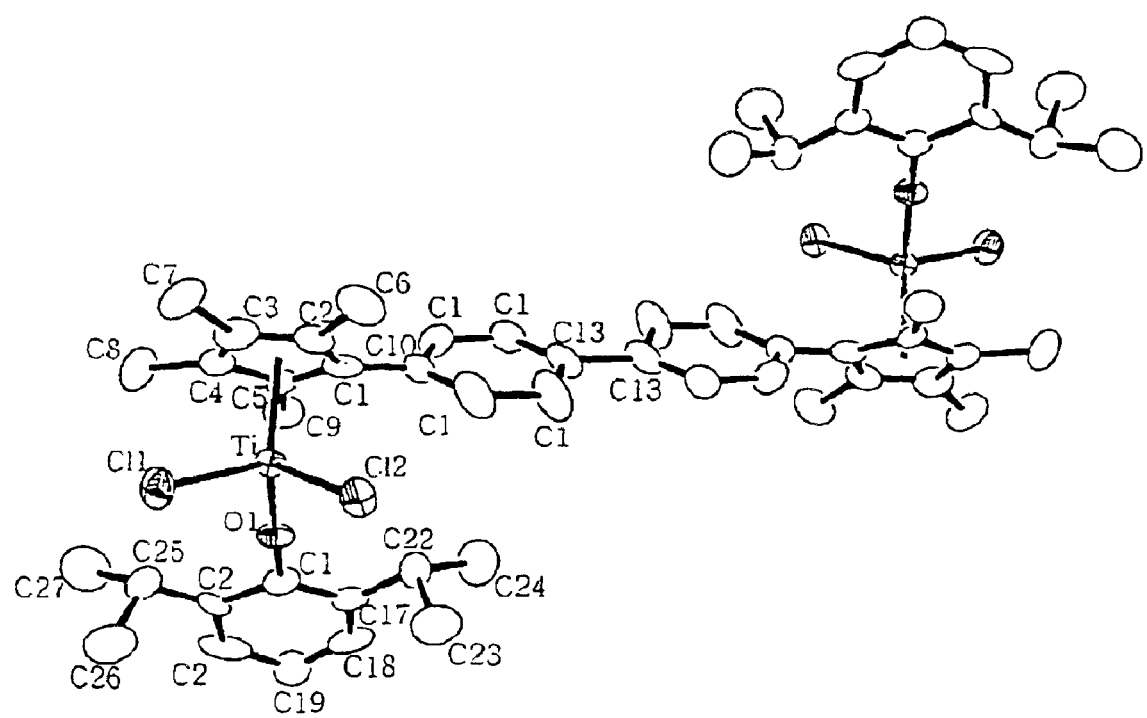
FIG. 2 shows an X-ray molecular structure of the compound prepared in Synthesis Example 3 of the present invention.

The synthesis process is presented in the following scheme 2, and the X-ray molecular structure of 4,4'-biphenylene bis(2,3,4,5-tetramethylcyclopentadienyl) di(2,6-diisopropylphenoxytitanium dichloride) is shown in FIG. 2.

[Scheme 2]

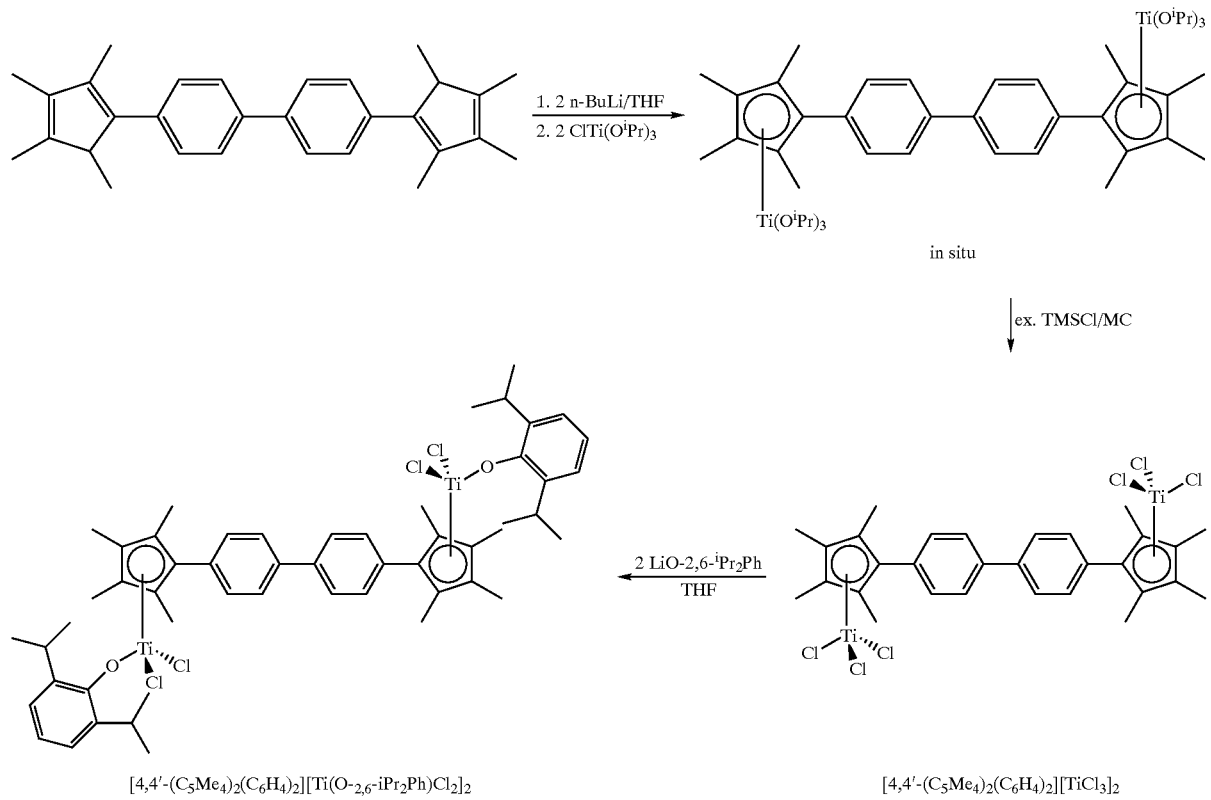

[4,4'-(C5Me4)2(C6H4)2][Ti(O-2,6-iPr2Ph)Cl2]2

[4,4'-(C5Me4)2(C6H4)2][TiCl3]2

Synthesis Example 4

1,2-bis[4-{(2,3,4,5-tetramethylcyclopentadienyl)(cyclopentadienyl)zirconium dichloride}phenyl]ethane (1,2-[4-{(C5Me4)CpZrCl2}C6H4]2(CH2CH2))

Synthesis Example 4-1

1,2-di(4-bromophenyl)ethane(1,2-(BrC6H4)2(CH2CH2))

4.718 g (20.0 mmol) of 1,4-bromobenzene was dissolved in 30 ml of diethylether, and the solution was cooled down to 0° C. 8.4 ml (1.1 equivalent, 21 mmol) of n-butyllithium was dropped into the solution with a syringe. The solution was stirred for 20 minutes at 0° C. and cooled down to −78° C. to form a white precipitate. After making the precipitate settle and discarding the supernatant, the precipitate was dissolved in 30 ml of tetrahydrofuran (THF) at −78° C. In a separate flask, 4.998 g (20.0 mmol) of 4-bromobenzyl bromide was dissolved in 20 ml of THF and the resulting solution was dropped into the precipitate solution with a cannular. The mixed solution was slowly warmed to the room temperature and stirred for more than 6 hours to form a light yellowish brown solution and terminate the reaction. After adding an appropriate amount of a saturated ammonium chloride aqueous solution, the organic layer was extracted with 50 ml (×3) of diethylether, dried on anhydrous magnesium sulfate and then filtered. The solution was removed of the solvent on a rotary evaporator and subjected to separation to obtain 2.890 g (85% yield) of a white solid product.

$^1$H NMR (400.13 MHz, CDCl$_3$): 7.36(d,4H), 6.96 (d, 4H), 2.82 (s, 4H).

Synthesis Example 4-2

1,2-di[4-(2,3,4,5-tetramethylcyclopentadienyl)phenyl]ethane(1,2-[4-(C5Me4H)C6H4]2(CH2CH2))

3.400 g (10 mmol) of 1,2-di(4-bromophenyl) ethane prepared in Synthesis Example 4-1 was dissolved in 50 ml of diethylether, and the solution was cooled down to 0° C. 8.4 ml (2.1 equivalents, 21 mmol) of n-butyllithium was dropped into the solution with a syringe. The solution was stirred for one hour at 0° C., slowly warmed to the room temperature and then stirred for more 2 hours to form a white precipitate. After malting the precipitate settle and discarding the supernatant, the precipitate was dissolved in 30 ml of THF at −78° C. In a separate flask, 2.764 g (20.0 mmol) of 2,3,4,5-tetramethyl-2-cyclopentenone was mixed with 20 ml of THF and the resulting solution was dropped into the precipitate solution with a cannular. The mixed solution was slowly warmed to the room temperature and stirred for more than 6 hours to form a light yellowish solution. After adding an appropriate amount of a saturated ammonium chloride aqueous solution, the organic layer was extracted with 50 ml (×3) of diethylether, dried on anhydrous magnesium sulfate and then filtered. The solution was removed of the solvent on a rotary evaporator to obtain a yellow sticky oil. This oil was dissolved in 50 ml of methylene chloride and then stirred with a catalytic amount (0.1 g) of p-toluene sulfonate hydrate at the room temperature for 2 hours to form a yellowish solid. With the solvent vaporized on the rotary evaporator until the solid was wet, the solid was washed with 30 ml of hexane and filtered out. The yellowish solid was washed with 30 ml (×3) of anhydrous ethanol and 30 ml (×2) of pentane and dried under vacuum to obtain 2.825 g (67% yield) of a yellowish solid.

$^1$H NMR (400.13 MHz, CDCl$_3$): 7.18(m, 8H), 3.17(q, 2H), 2.93(m, 4H), 2.02(s, 6H), 1.91(s, 6H), 1.85(s, 6H), 0.95(d, 6H). $^{13}$C{$^1$H} NMR (1.00.62 MHz, CDCl$_3$): 142.7, 140.4, 139.0, 136.7, 135.0, 134.8, 128.4, 18.1, 50.1, 37.6, 14.9, 12.7, 11.9, 11.1.

Synthesis Example 4-3

1,2-bis[4-{(2,3,4,5-tetramethylcyclopentadienyl) (cyclopentadienyl)zirconium dichloride}phenyl] ethane (1,2-[4-{(C$_5$Me$_4$)CpZrCl$_2$}C$_6$H$_4$]$_2$(CH$_2$CH$_2$))

0.422 g (1.0 mmol) of 1,2-di[4-(2,3,4,5-tetramethylcyclopentadienyl)phenyl]ethane prepared in Synthesis Example 4-2 was dissolved in 30 ml of THF, and the solution was cooled down to −78° C. 1.0 ml (2.5 equivalents, 2.5 mmol) of n-butyllithium was dropped into the solution with a syringe. The solution was slowly warmed to the room temperature and stirred for 4 hours to form a yellowish precipitate. In a separate flask, 0.525 g (2.0 mmol) of cyclopentadienylzirconium trichloride was dissolved in 20 ml of THF and the resulting solution was slowly dropped into the precipitate solution with a cannular at −78° C. The mixed solution was slowly warmed to the room temperature and stirred for more than 24 hours to form a yellowish clear solution. The solution was dried under vacuum to evaporate the solvent to obtain a solid, which was dissolved in toluene and removed of the remaining LiCl by celite-based filtration. The resulting solution was dried under vacuum and, after adding an appropriate amount of pentane, cooled down to obtain 0.642 g (73% yield) of a yellowish solid.

$^1$H NMR (400.13 MHz, CDCl$_3$): 7.20 (d, 4H), 7.05 (d, 4H), 6.13 (s, 10H), 2.99 (s, 4H), 2.22 (s, 12H), 2.05 (s, 12H). $^{13}$C{$^1$H} NMR (100.62 MHz, CDCl$_3$): 140.6, 131.7, 129.7, 128.5, 126.5, 126.1, 124.2, 116.7, 37.3, 13.9, 12.3.

Anal. Calcd for C$_{42}$H$_{46}$Cl$_4$Zr$_2$: C, 57.65; H, 5.30. Found: C, 57.96; H, 5.81.

Figure 3:
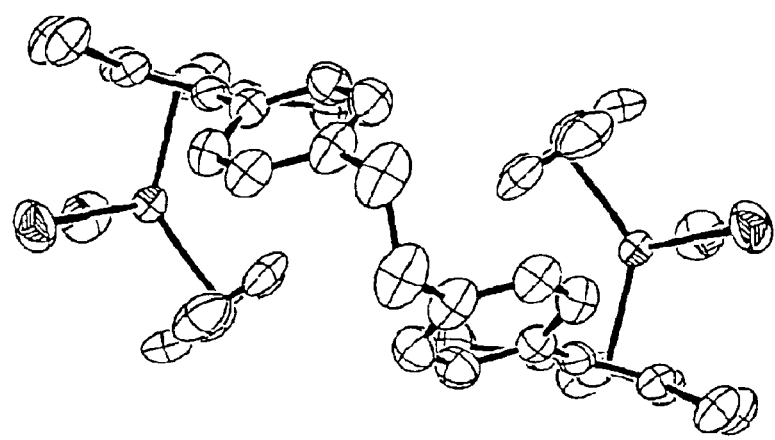
FIG. 3 shows an X-ray molecular structure of the compound prepared in Synthesis Example 4 of the present invention.
Figure 3:
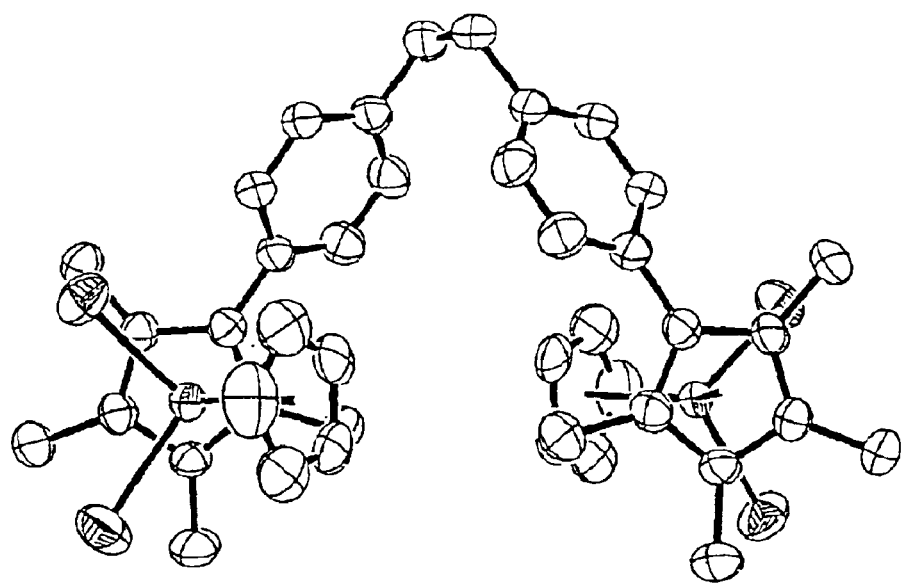

The synthesis process is presented in the following scheme 3, and the X-ray molecular structure of 1,2-bis[4-{ (2,3,4,5-tetramethylcyclopentadienyl)(cyclopentadienyl) zirconium dichloride}phenyl]ethane is shown in FIG. 3.

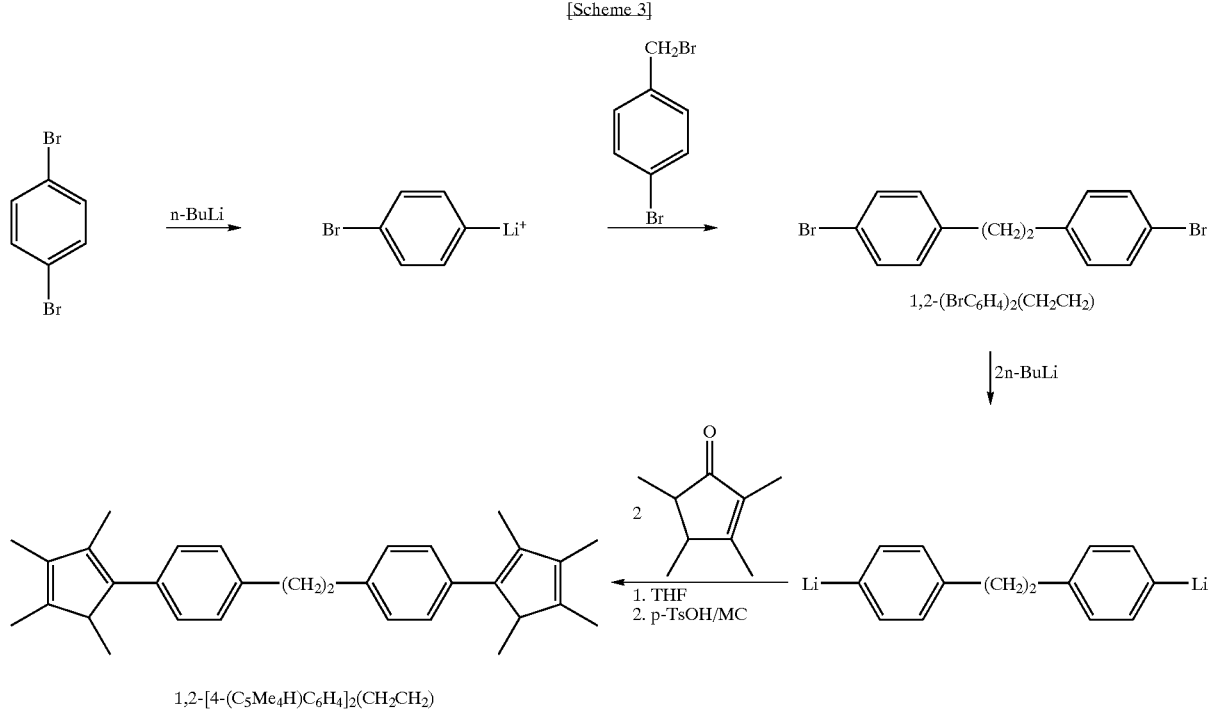

[Scheme 3]

-continued

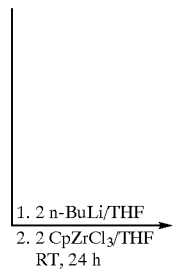
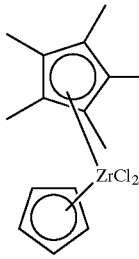

1. 2 n-BuLi/THF
2. 2 CpZrCl$_3$/THF
RT, 24 h 1,2-[4-{(C$_5$Me$_4$)CpZrCl$_2$}C$_6$H$_4$]$_2$(CH$_2$CH$_2$)

Synthesis Example 5

1,2-bis[4-{(3,4-dimethylcyclopentadienyl)(cyclopentadienyl)zirconium dichloride}phenyl]ethane (1,2-[4-{(C$_5$Me$_2$H$_2$)CpZrCl$_2$}C$_6$H$_4$]$_2$(CH$_2$CH$_2$))

Synthesis Example 5-1

1,2-bis[4-(3,4-dimethylcyclopentadienyl)phenyl]ethane (1,2-[4-(C$_5$Me$_2$H$_3$)C$_6$H$_4$]$_2$(CH$_2$CH$_2$))

3.400 g (10 mmol) of 1,2-di(4-bromophenyl) ethane prepared in Synthesis Example 4-1 was dissolved in 50 ml of diethylether, and the solution was cooled down to 0° C. 8.4 ml (2.1 equivalents, 21 mmol) of n-butyllithium was dropped into the solution with a syringe. The solution was stirred for one hour at 0° C., slowly warmed to the room temperature and then stirred for more 2 hours to form a white precipitate. After making the precipitate settle and discarding the supernatant, the precipitate was dissolved in 30 ml of THF at –78° C. In a separate flask, 2.183 g (20.0 mmol) of 3,4-dimethyl-2-cyclopentenone was mixed with 20 ml of THF and the resulting solution was slowly dropped into the precipitate solution with a cannular. The mixed solution was slowly warmed to the room temperature and stirred for more than 6 hours to form a light yellowish solution. After adding an appropriate amount of a saturated ammonium chloride aqueous solution to terminate the reaction, the organic layer was extracted with 50 ml (×3) of diethylether, dried on anhydrous magnesium sulfate and then filtered. The solution was removed of the solvent on a rotary evaporator to obtain a yellowish sticky oil. This oil was dissolved in 50 ml of methylene chloride and mixed Faith a catalytic amount (0.1 g) of p-toluene sulfonate hydrate. The resulting solution was stirred for 2 hours at the room temperature to form a light brown solid. With the solvent vaporized on the rotary evaporator until the solid was wet, the solid was washed with 30 ml of hexane and filtered out. The solid was washed with 30 ml (×3) of anhydrous ethanol and 30 ml (×2) of pentane and dried under vacuum to obtain 2.314 g (63% yield) of an ivory solid.

$^1$H NMR (400.13 MHz, CDCl$_3$): 7.35 (d, 4H), 7.09 (d, 4H), 6.60 (s, 2H), 3.24 (s, 4H), 2.86 (s, 4H), 1.96 (s, 6H), 1.87 (s, 6H). $^{13}$C{$^1$H} NMR (100.62 MHz, CDCl$_3$): 142.4, 139.7, 135.5, 135.4, 134.2, 131.0, 128.6, 124.5, 45.3, 37.6, 13.4, 12.6.

Synthesis Example 5-2

1,2-bis[4-{(3,4-dimethylcyclopentadienyl)(cyclopentadienyl)zirconium dichloride}phenyl]ethane (1,2-[4-{(C$_5$Me$_2$H$_2$)CpZrCl$_2$}C$_6$H$_4$]$_2$(CH$_2$CH$_2$))

0.367 g (1.00 mmol) of 1,2-bis[4-(3,4-dimethylcyclopentadienyl)phenyl]ethane prepared in Synthesis Example 5-1 was dissolved in 30 ml of THF, and the solution was cooled down to –78° C. 1.0 ml (2.5 equivalents, 2.5 mmol) of n-butyllithium was dropped into the solution with a syringe. The solution was slowly warmed to the room temperature and stirred for more 4 hours to form an ivory precipitate. In a separate flask, 0.525 g (2.0 mmol) of cyclopentadienylzirconium trichloride was dissolved in 20 ml of THF and the resulting solution was slowly dropped into the precipitate solution with a cannular at –78° C. The mixed solution was slowly warmed to the room temperature and stirred for more than 24 hours to form a light yellowish solution. After vaporizing the solvent under vacuum, the solid thus obtained was dissolved in toluene and removed of the remaining LiCl by celite-based filtration. The resulting solution was dried under vacuum and, after adding an appropriate amount of pentane, cooled down to obtain 0.572 g (70% yield) of a light yellowish solid.

$^1$H NMR (400.13 MHz, CDCl$_3$): 7.35 (d, 4H), 7.12 (d, 4H), 6.50 (s, 4H), 6.11 (s, 10H), 2.97 (s, 4H), 2.14 (s, 12H). $^{13}$C{$^1$H} NMR (100.62 MHz, CDCl$_3$): 140.8, 131.4, 129.4, 128.2, 125.1, 124.5, 116.5, 114.0, 37.3, 13.8.

Anal. Calcd for C$_{38}$H$_{38}$Cl$_4$Zr$_2$: C, 55.74; H. 4.68. Found: C, 56.98; H, 5.18.

The synthesis process is presented in the following scheme 4.

[Scheme 4]

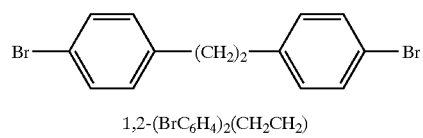

1,2-(BrC$_6$H$_4$)$_2$(CH$_2$CH$_2$)

2n-BuLi →

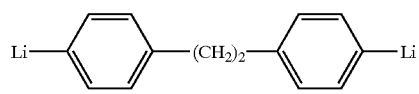

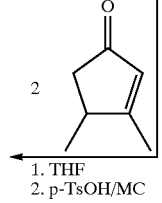

1. THF
2. p-TsOH/MC

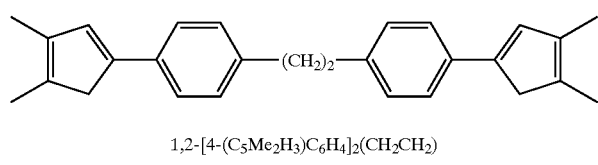

1,2-[4-(C$_5$Me$_2$H$_3$)C$_6$H$_4$]$_2$(CH$_2$CH$_2$)

1. 2 n-BuLi/THF
2. 2 CpZrCl$_3$/THF
   RT, 24 h

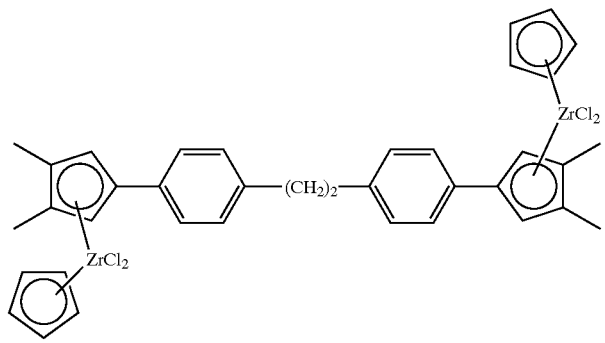

1,2-[4-{(C$_5$Me$_2$H$_2$)CpZrCl$_2$}C$_6$H$_4$]$_2$(CH$_2$CH$_2$)

Synthesis Example

Supported Catalyst 20 ml of toluene was added to 1 g of silica (Grace Davison #2412) calcinated in the nitrogen atmosphere at 800° C. for 12 hours. 2.38 ml (11.16 mmol) of methyl aluminoxane (MMAO, Witco AL 5100/30T) was added at the room temperature, and the resulting solution was stirred for 10 minutes. After adding 0.09 g (0.11 mmol) of 4,4'-biphenylene bis(2,3,4,5-tetramethylcyclopentadienyl) di(cyclopentanedienylzirconium dichloride) prepared in Synthesis Example 1, the solution was stirred for one hour and, after stopping the reaction, toluene was vaporized at the room temperature. The supported catalyst thus obtained was washed with an excess of toluene and the remaining toluene was completely vaporized at the room temperature to obtain a light yellowish green free flowing supported catalyst in the solid state, which was then dried at 50° C. for more 30 minutes.

Comparative Synthesis Example

Supported Catalyst

The procedures were performed in the same manner as described in Synthesis Example of Supported Catalyst, excepting that 0.032 g of bis(cyclopentadienylzirconium) dichloride (Cp$_2$ZrCl$_2$) was used instead of 0.09 g of 4,4'-biphenylene bis(2,3,4,5-tetramethylcyclopentadienyl) di(cyclopentanedienylzirconium dichloride).

Polymerization Examples

Polymerization Example Using Non-Supported Catalyst

All the polymerization reactions were performed under a predetermined ethylene pressure after injecting a defined amount of hydrogen, 1-hexene and catalyst in an airtight autoclave. The molecular weight and the molecular weight distribution of the polymers thus obtained were measured by the gel permeation chromatography (GPC, PL-GPC220), and the melting point was measured by the differential scanning calorimetry (DSC, TA Instruments).

Polymerization Example 1

After introducing nitrogen into a stainless autoclave having an inner volume of 2 liters and adding 600 ml of toluene, there were sequentially added 2 mmol of methyl aluminoxane (MAO (Witco, TA 02258/10HP)) based on the Al atom and 0.5 µmol of 4,4'-biphenylene bis(2,3,4,5-tetramethylcyclopentadienyl) di(cyclopentanedienylzirconium dichloride) prepared in Synthesis Example 1. The solution was heated to 60° C. and, after introducing an ethylene gas, the polymerization reaction was performed for one hour at 70° C. with the total pressure of 6 bar·g. 50 ml of 10% HCl/MeOH was added to terminate the polymerization reaction and the polymer thus obtained was washed with an excess of methanol and dried under vacuum at 60° C. for 15 hours. The polymerization results are presented in Table 1.

Polymerization Example 2

The procedures for ethylene polymerization were performed in the same manner as described in Polymerization Example 1, excepting that 0.03 bar of hydrogen was introduced for polymerization.

Polymerization Example 3

The procedures for ethylene polymerization were performed in the same manner as described in Polymerization Example 1, excepting that 0.1 bar of hydrogen was introduced for polymerization.

Polymerization Example 4

The procedures for ethylene polymerization were performed in the same manner as described in Polymerization Example 1, excepting that 0.4 bar of hydrogen was introduced for polymerization.

Polymerization Example 5

The procedures for ethylene polymerization were performed in the same manner as described in Polymerization Example 1, excepting that 1.2 bar of hydrogen was introduced for polymerization.

Polymerization Example 6

The procedures for ethylene polymerization were performed in the same manner as described in Polymerization Example 1, excepting that 10 ml of 1-hexene was added for polymerization.

Polymerization Example 7

The procedures for ethylene polymerization were performed in the same manner as described in Polymerization Example 1, excepting that 30 ml of 1-hexene was added for polymerization.

Polymerization Example 8

The procedures for ethylene polymerization were performed in the same manner as described in Polymerization Example 1, excepting that 50 ml of 1-hexene was added for polymerization.

Polymerization Example 9

The procedures for ethylene polymerization were performed in the same manner as described in Polymerization Example 1, excepting that 0.1 bar of hydrogen and 30 ml of 1-hexene were introduced for polymerization.

Polymerization Example 10

The procedures for ethylene polymerization were performed in the same manner as described in Polymerization Example 1, excepting that 600 ml of n-hexane was used as a solvent instead of toluene.

Polymerization Example 11

The procedures for ethylene polymerization were performed in the same manner as described in Polymerization Example 10, excepting that the polymerization temperature was 60° C.

Polymerization Example 12

The procedures for ethylene polymerization were performed in the same manner as described in Polymerization Example 10, excepting that the polymerization temperature was 80° C.

Polymerization Example 13

The procedures for ethylene polymerization were performed in the same manner as described in Polymerization Example 10, excepting that the polymerization temperature was 90° C.

Polymerization Example 14

The procedures for ethylene polymerization were performed in the same manner as described in Polymerization Example 1, excepting that 4,4'-biphenylene bis(2,3,4,5-tetramethylcyclopentadienyl) di(titanium trichloride) prepared in Synthesis Example 2 was used instead of 4,4'-biphenylene bis(2,3,4,5-tetramethylcyclopentadienyl) di(cyclopentanedienylzirconium dichloride).

Polymerization Example 15

The procedures for ethylene polymerization were performed in the same manner as described in Polymerization Example 1, excepting that 4,4'-biphenylene bis(2,3,4,5-tetramethylcyclopentadienyl) di(2,6-diisopropylphenoxytitanium dichloride) prepared in Synthesis Example 3 was used instead of 4,4'-biphenylene bis(2,3,4,5-tetramethylcyclopentadienyl) di(cyclopentanedienylzirconium dichloride).

Polymerization Example 16

The procedures for ethylene polymerization were performed in the same manner as described in Polymerization Example 1, excepting that 1,2-bis[4-{(2,3,4,5-tetramethylcyclopentadienyl)(cyclopentadienyl)zirconium dichloride}phenyl]ethane prepared in Synthesis Example 4 was used instead of 4,4'-biphenylene bis(2,3,4,5-tetramethylcyclopentadienyl) di(cyclopentanedienylzirconium dichloride).

Polymerization Example 17

The procedures for ethylene polymerization were performed in the same manner as described in Polymerization Example 16, excepting that 600 ml of n-hexane was used as a solvent instead of toluene.

Polymerization Example 18

The procedures for ethylene polymerization were performed in the same manner as described in Polymerization Example 17, excepting that 0.1 bar of hydrogen was introduced for polymerization.

Polymerization Example 19

The procedures for ethylene polymerization were performed in the same manner as described in Polymerization Example 17, excepting that 0.4 bar of hydrogen was introduced for polymerization.

Polymerization Example 20

The procedures for ethylene polymerization were performed in the same manner as described in Polymerization Example 17, excepting that 1.2 bar of hydrogen was introduced for polymerization.

Polymerization Example 21

The procedures for ethylene polymerization were performed in the same manner as described in Polymerization Example 17, excepting that the polymerization temperature was 60° C.

Polymerization Example 22

The procedures for ethylene polymerization were performed in the same mauler as described in Polymerization Example 17, excepting that the polymerization temperature was 80° C.

Polymerization Example 23

The procedures for ethylene polymerization were performed in the same manner as described in Polymerization Example 17, excepting that the polymerization temperature was 90° C.

Polymerization Example 24

The procedures for ethylene polymerization were performed in the same manner as described in Polymerization Example 1, excepting that 1,2-bis[4-{(3,4-dimethylcyclopentadienyl)(cyclopentadienyl)zirconium dichloride}phenyl] ethane prepared in Synthesis Example 5 was used instead of 4,4'-biphenylene bis(2,3,4,5-tetramethylcyclopentadienyl) di(cyclopentanedienylzirconium dichloride).

Comparative Polymerization Example 1

The procedures for ethylene polymerization were performed in the same manner as described in Polymerization Example 1, excepting that 1.0 μmol of bis(cyclopentadienyl) zirconium dichloride ($Cp_2ZrCl_2$) was used instead of 4,4'-biphenylene bis(2,3,4,5-tetramethylcyclopentadienyl) di(cyclopentanedienylzirconium dichloride).

Comparative Polymerization Example 2

The procedures for ethylene polymerization were performed in the same manner as described in Comparative Polymerization Example 1, excepting that n-hexane was used instead of toluene.

Comparative Polymerization Example 3

The procedures for ethylene polymerization were performed in the same manner as described in Comparative Polymerization Example 1, excepting that pentamethylcyclopentadienyltitanium trichloride ($CpTiCl_3$) was used instead of biscyclopentadienylzirconium dichloride.

Polymerization Example Using Supported Catalyst

After introducing nitrogen into a stainless autoclave having an inner volume of 2 liters and adding 600 ml of n-hexane, there were sequentially added 2 mmol of triethylaluminum and 0.05 g of the supported catalyst prepared in Synthesis Example of Supported Catalyst. The solution was heated to 60° C. and, after introducing an ethylene gas, the polymerization reaction was performed for one hour at 70° C. with the total pressure of 6 bar·g. 50 ml of 10% HCl/MeOH was added to terminate the polymerization reaction and the polymer thus obtained was washed with an excess of methanol and dried under vacuum at 60° C. for 15 hours. The polymerization results are presented in Table 2.

Comparative Polymerization Example Using Supported Catalyst

The procedures for ethylene polymerization were performed in the same manner as described in Polymerization Example Using Supported Catalyst, excepting that the supported catalyst prepared in Comparative Synthesis Example of Supported Catalyst was used. The polymerization results are presented in Table 2.

TABLE 1

Results of polymerization using non-supported catalyst.

| | | Catalyst | Solvent | Hydrogen (bar) | 1-Hexene (ml) | Activity[e] | C | D | E |
|---|---|---|---|---|---|---|---|---|---|
| A[a] | 1 | Synthesis Example 1 | T[c] | 0 | 0 | 47.2 | 828 | 2.68 | 138.5 |
| | 2 | Synthesis Example 1 | T | 0.03 | 0 | 73.6 | 101 | 3.76 | 136.9 |
| | 3 | Synthesis Example 1 | T | 0.1 | 0 | 51.0 | 55.5 | 5.46 | 136.6 |
| | 4 | Synthesis Example 1 | T | 0.4 | 0 | 49.1 | 34.3 | 9.17 | 133.4 |
| | 5 | Synthesis Example 1 | T | 1.2 | 0 | 30.2 | 65.4 | 53.0 | 127.9 |
| | 6 | Synthesis Example 1 | T | 0 | 10 | 20.8 | 721 | 3.35 | 131.8 |
| | 7 | Synthesis Example 1 | T | 0 | 30 | 64.1 | 661 | 2.29 | 125.7 |
| | 8 | Synthesis Example 1 | T | 0 | 50 | 41.5 | 552 | 3.41 | 122.6 |
| | 9 | Synthesis Example 1 | T | 0.1 | 30 | 90.6 | 237 | 2.91 | 126.8 |
| | 10 | Synthesis | H[d] | 0 | 0 | 26.4 | 712 | 2.97 | 141.0 |

TABLE 1-continued

Results of polymerization using non-supported catalyst.

|   |    | Catalyst | Solvent | Hydrogen (bar) | 1-Hexene (ml) | Activity[e] | C | D | E |
|---|----|----------|---------|----------------|---------------|-------------|---|---|---|
|   | 11 | Synthesis Example 1 | H | 0 | 0 | 24.5[f] | 916 | 2.52 | 135.3 |
|   | 12 | Synthesis Example 1 | H | 0 | 0 | 24.5[g] | 586 | 2.53 | 139.1 |
|   | 13 | Synthesis Example 1 | H | 0 | 0 | 9.43[h] | 391 | 3.10 | 137.5 |
|   | 14 | Synthesis Example 1 | T | 0 | 0 | 6.5 | 457 | 2.82 | 136.1 |
|   | 15 | Synthesis Example 2 | T | 0 | 0 | 7.8 | 528 | 3.01 | 136.7 |
|   | 16 | Synthesis Example 3 | T | 0 | 0 | 45.1 | 1,250 | 2.57 | 140.0 |
|   | 17 | Synthesis Example 4 | H | 0 | 0 | 25.1 | 1,089 | 2.42 | 137.7 |
|   | 18 | Synthesis Example 4 | H | 0.1 | 0 | 24.1 | 172 | 4.6 | 136.0 |
|   | 19 | Synthesis Example 4 | H | 0.4 | 0 | 20.8 | 138 | 7.5 | 136.0 |
|   | 20 | Synthesis Example 4 | H | 1.2 | 0 | 20.8 | 80 | 11.0 | 133.6 |
|   | 21 | Synthesis Example 4 | H | 0 | 0 | 24.3[f] | 1,320 | 2.48 | 140.5 |
|   | 22 | Synthesis Example 4 | H | 0 | 0 | 23.8[g] | 607 | 2.52 | 139.6 |
|   | 23 | Synthesis Example 4 | H | 0 | 0 | 11.3[h] | 412 | 2.61 | 137.8 |
|   | 24 | Synthesis Example 5 | T | 0 | 0 | 46.2 | 1,137 | 2.8 | 140.5 |
| B[b] | 1 | $Cp_2ZrCl_2$ | T | 0 | 0 | 38.7 | 241 | 2.12 | 139.9 |
|   | 2 | $Cp_2ZrCl_2$ | H | 0 | 0 | 16.0 | 384 | 3.76 | 139.3 |
|   | 3 | $CpTiCl_3$[i] | T | 0 | 0 | 3.5 | 103 | 2.75 | 136.1 |

A: Example
B: Comparative Example
C: Molecular weight (Mw) (×10⁻³)
D: Molecular weight distribution (Mw/Mn)
E: Melting point of polymer (° C.)
[a]Polymerization Condition: P (ethylene), 6 bar; Tp 70° C.; tp, 1 h; [catalyst] 0.5 μmol; [Al]/[Zr], 2000
[b][catalyst], 1.0 μmol; [Al]/[Zr], 2000
[c]T, 600 ml toluene
[d]H, 600 ml n-hexane
[e]Activity, (10³ kg of Polymer)/(mol of Zr) · h
[f]Tp, 60 ° C.
[g]Tp, 80 ° C.
[h]Tp, 90 ° C.
[i]Activity, (10³ kg of Polymer)/(mol of Ti) · h

TABLE 2

Results of polymerization using supported catalyst.

|   | Supported Catalyst | Solvent | Hydrogen (bar) | 1-Hexene (ml) | Activity[b] | C | D | E |
|---|--------------------|---------|----------------|---------------|-------------|---|---|---|
| A[a] | Synthesis Example | H[c] | 0 | 0 | 1.8 | 652 | 3.85 | 138.5 |
| B | Comparative Example | H | 0 | 0 | 0.8 | 92.3 | 3.52 | 136.9 |

A: Example
B: Comparative Example
C: Molecular weight (Mw) (×10⁻³)
D: Molecular weight distribution (Mw/Mn)
E: Melting point of polymer (° C.)
[a]Polymerization Condition: P (ethylene), 6 bar; Tp 70° C.; tp, 1 h; [supported catalyst] 0.05 g; TEA 2 mmole
[b]Activity, (kg of Polymer)/(g of Cat.) · h
[c]H, 600 ml n-hexane

INDUSTRIAL APPLICABILITY

As described above, the catalyst for olefin polymerization according to the present invention comprises, as a main catalyst, a transition metal compound that contains at least two metal atoms in the groups III to X of the periodic table as central metals and a ligand having a cyclopentadienyl structure bridging between the two metal atoms, and, as a cocatalyst, an aluminoxane compound, an organoaluminum compound or a bulky compound reactive to the transition metal compound to impart a catalytic activity to the transition metal compound, thereby effectively producing polyolefin having various molecular weights and various molecular weight distributions.

What is claimed is:

1. A multinuclear catalyst for olefin polymerization comprising:

(A) a transition metal compound represented by the formula 1:

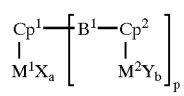
   [Formula 1]

wherein $M^1$ and $M^2$ are the same or different and each represents an element in the groups III to X of the periodic table; $Cp^1$ and $Cp^2$ are the same or different and each represents a ligand having an unsubstituted or substituted cyclopentadienyl structure, the substituted cyclopentadienyl structure having at least one substituent selected from the group consisting of a $C_1$–$C_{20}$ alkyl group, a $C_3$–$C_{20}$ cycloalkyl group, a $C_1$–$C_{20}$ alkylsilyl group, a $C_1$–$C_{20}$ haloalkyl group, a $C_6$–$C_{20}$ aryl group, a $C_7$–$C_{20}$ arylalkyl group, a $C_6$–$C_{20}$ arylsilyl group, a $C_7$–$C_{20}$ alkylaryl group, a $C_1$–$C_{20}$ alkoxy group, a $C_1$–$C_{20}$ alkylsiloxy group, a $C_6$–$C_{20}$ aryloxy group, a halogen atom and an amino group; and $B^1$ represents a $C_{12}$–$C_{40}$ arylene group or an arylene group represented by the formula 2:

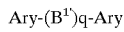
   [Formula 2]

wherein Ary represents a $C_6$–$C_{20}$ arylene group directly bonded to $Cp^1$ and $Cp^2$; $B^{1'}$ represents a $C_1$–$C_{20}$ alkylene group, a $C_3$–$C_{20}$ cycloalkylene group, a $C_1$–$C_{20}$ alkylsilylene group, a $C_1$–$C_{20}$ haloalkylene group, a $C_7$–$C_{20}$ arylalkylene group or a $C_6$–$C_{20}$ arylsilylene group; and q is an integer from 0 to 5;

X and Y are the same or different and each represents $Cp^1$ or $Cp^2$, a $C_1$–$C_{20}$ alkyl group, a $C_3$–$C_{20}$ cycloalkyl group, a $C_1$–$C_{20}$ alkylsilyl group, a $C_1$–$C_{20}$ haloalkyl group, a $C_6$–$C_{20}$ aryl group, a $C_7$–$C_{20}$ arylalkyl group, a $C_6$–$C_{20}$ arylsilyl group, a $C_6$–$C_{20}$ alkylaryl group, a $C_1$–$C_{20}$ alkoxy group, a $C_1$–$C_{20}$ alkylsiloxy group, a $C_6$–$C_{20}$ aryloxy group, a halogen atom, an amino group or a tetrahydroborate group; a and b are an integer from 1 to 5 determined by the oxidation number of the central metal; and p is an integer from 1 to 3; and (B) an aluminoxane compound represented by the formula 9, an organoaluminum compound represented by the formula 10, or bulky compound represented by the formula 11 that is reactive to the transition metal compound to impart a catalytic activity to the transition metal compound:

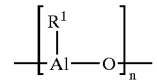
   [Formula 9]

wherein $R^1$ represents a $C_1$–$C_{10}$ alkyl group; and n is an integer from 2 to 70;

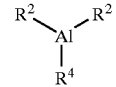
   [Formula 10]

wherein $R^2$, $R^3$ and $R^4$ are the same or different and each represents a $C_1$–$C_{10}$ alkyl group, a $C_1$–$C_{10}$ alkoxy group or a halide group, at least one of $R^2$, $R^3$ and $R^4$ is an alkyl group; and

[C][D]     [Formula 11]

wherein C represents a proton-bonded cation of a Lewis base, or an oxidative metallic or non-metallic compound; and D is a compound of an element in the groups V to XV of the Periodic Table of the Elements and an organic substance.

2. The multinuclear catalyst for olefin polymerization as claimed in claim 1, wherein the transition metal compound (A) is represented by the formula 3:

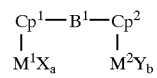

wherein $M^1$, $M^2$, $Cp^1$, $Cp^2$, $B^1$, X, Y, a and b are the same as defined the formula 1.

3. The multinuclear catalyst for olefin polymerization as claimed in claim 1, wherein $M^1$ and $M^2$ are an element in the group IV of the periodic table.

4. The multinuclear catalyst for olefin polymerization as claimed in claim 1, wherein the substituent of the cyclopentadienyl structure of $Cp^1$ and $Cp^2$ is at least one selected from the group consisting of methyl, ethyl, propyl, butyl, pentyl, hexyl, cyclopropyl, cyclobutyl, cyclopentyl, cyclohexyl, methylsilyl, dimethylsilyl, trimethylsilyl, ethylsilyl, diethylsilyl, triethylsilyl, propylsilyl, dipropylsilyl, tripropylsilyl, butylsilyl, dibutylsilyl, tributylsilyl, trifluoromethyl, phenyl, biphenyl, terphenyl, naphthyl, fluorenyl, benzyl, phenylethyl, phenylpropyl, phenylsilyl, phenyldimethylsilyl, diphenylmethylsilyl, triphenylsilyl, methylphenyl, dimethylphenyl, trimethylphenyl, ethylphenyl, diethylphenyl, triethylphenyl, propylphenyl, dipropylphenyl, tripropylphenyl, methoxy, ethoxy, propoxy, butoxy, pentoxy, hexyloxy, methylsiloxy, dimethylsiloxy, trimethylsiloxy, ethylsiloxy, diethylsiloxy, triethylsiloxy, phenoxy, naphthoxy, methylphenoxy, dimethylphenoxy, trimethylphenoxy, ethylphenoxy, diethylphenoxy, triethylphenoxy, propylphenoxy, dipropylphenoxy, tripropylphenoxy, fluorine, chlorine, bromine, iodine, dimethylamino, diethylamino, dipropylamino, dibutylamino, diphenylamino, and dibenzylamino.

5. The multinuclear catalyst for olefin polymerization as claimed in claim 1, wherein $Cp^1$ and $Cp^2$ are cyclopentadienyl, methylcyclopentadienyl, dimethylcyclopentadienyl, trimethylcyclopentadienyl, tetramethylcyclopentadienyl, ethylcyclopentadienyl, diethylcyclopentadienyl, triethylcyclopentadienyl, n-propylcyclopentadienyl, iso-propylcyclopentadienyl, n-butylcyclopentadienyl, iso-butylcyclopentadienyl, tert-butylcyclopentadienyl, indenyl, methylindenyl, dimethylindenyl, trimethylindenyl, ethylindenyl, diethylindenyl, or triethylindenyl.

6. The multinuclear catalyst for olefin polymerization as claimed in claim 1, wherein the arylene group of $B^1$ is with or without heteroatom, and selected from biphenylene, terphenylene, naphthylene, binaphthylene, fluorenylene, anthracylene, pyridylene, bipyridylene, terpyridylene, quinolylene, pyridazylene, pyrimidylene, pyrazylene, or quinoxalylene.

7. The multinuclear catalyst for olefin polymerization as claimed in claim 1, wherein at least one of X and Y is a cyclopentadienyl, methylcyclopentadienyl, dimethylcyclopentadienyl, trimethylcyclopentadienyl, tetramethylcyclopentadienyl, pentamethylcyclopentadienyl, ethylcyclopentadienyl, diethylcyclopentadienyl, triethylcyclopentadienyl, n-propylcyclopentadienyl, iso-propylcyclopentadienyl, n-butylcyclopentaienyl, iso-butylcyclopentaienyl, tert-butylcyclopentaienyl, indenyl, methylindenyl, dimethylindenyl, trimethylindenyl, ethylindenyl, diethylindenyl, triethylindenyl, phenoxy, naphthoxy, methylphenoxy, dimethylphenoxy, trimethylphenoxy, ethylphenoxy, diethylphenoxy, triethylphenoxy, propylphenoxy, dipropylphenoxy, tripropylphenoxy, fluorine, chlorine, bromine, iodine, dimethylamino, diethylamino, dipropylamino, dibutylamino, diphenylamino, and dibenzylamino.

8. The multinuclear catalyst for olefin polymerization as claimed in claim 1, wherein the aluminoxane compound (B) is methylaluminoxane, ethylaluminoxane, butylaluminoxane, isobutylaluminoxane, hexylaluminoxane, octylaluminoxane, or decylaluminoxane.

9. The multinuclear catalyst for olefin polymerization as claimed in claim 1, wherein the organoaluminium compound (B) is trialkylaluminum selected from the group consisting of trimethylaluminum, triethylaluminum, tributylaluminum triisobutylaluminum, trihexylaluminum, trioctylaluminum and tridecylaluminum and mixtures thereof;

dialkylaluminum alkoxide selected from the group consisting of dimethylaluminum methoxide, diethylaluminum methoxide, dibutylaluminum methoxide and diisobutylaluminum methoxide and mixtures thereof;

dialkylaluminum halide selected from the group consisting of dimethylaluminum chloride, diethylaluminum chloride, dibutylaluminum chloride and diisobutylaluminum chloride and mixtures thereof;

alkylaluminum dialkoxide selected from the group consisting of methylaluminum dimethoxide, ethylaluminum dimethoxide, butylaluminum dimethoxide and isobutylaluminum dimethoxide and mixtures thereof; or alkylaluminum dihalide selected from the group consisting of methylaluminum dichloride, ethylaluminum dichloride, butyaluminum dichloride and isobutylaluminum dichloride and mixtures thereof.

10. The multinuclear catalyst for olefin polymerization as claimed in claim 1, wherein the bulky compound (B) reactive to the transistion metal compound to impart a catalytic activity to the transition metal compound is trimethylammonium tetraphenylborate, triethylammonium tetraphenylborate, tripropylammonium tetraphenylborate, tributylammonium tetraphenylborate, trimethylammonium tetrakis(pentafluorophenyl)borate, triethylammonium tetrakis(pentafluorophenyl)borate, tripropylammonium tetrakis(pentafluorophenyl)borate, tributylammonium tetrakis(pentafluorophenyl)borate, anilium tetraphenylborate, anilium tetrakis(pentafluorophenyl)borate, pyridinium tetraphenyborate, pyridinium tetrakis(pentafluorophenyl)borate, ferrocenium tetrakis(pentafluorophenyl)borate, silver tetraphenylborate, silver tetrakis (pentafluorophenyl)borate, tris(pentafluorophenyl)borane, tris(2,3,5,6-tetrafluorophenyl)borane, or tris(3,4,5-trifluorophenyl)borane.

11. A supported catalyst for olefin polymerization comprising the multinuclear catalyst for olefin polymerization according to claim 1 supported on an organic or inorganic support.

12. A supported catalyst for olefin polymerization as claimed in claim 11, wherein the inorganic support is silica, alumina, bauxite, zeolite, $MgCl_2$, $CaCl_2$, MgO, $ZrO_2$, $TiO_2$, $B_2O_3$, CaO, ZnO, BaO, $ThO_2$, or a mixture thereof.

13. A method for olefin polymerization comprising polymerizing olefins using the catalyst according to claim 1.

14. A method for olefin polymerization comprising polymerizing olefins using the supported catalyst according to claim 11.

15. The multinuclear catalyst for olefin polymerization as claimed in claim 2, wherein $M^1$ and $M^2$ are an element in the group IV of the periodic table.

16. The multinuclear catalyst for olefin polymerization as claimed in claim 2, wherein the substituent of the cyclopentadienyl structure of $Cp^1$ and $Cp^2$ is at least one selected from the group consisting of methyl, ethyl, propyl, butyl, pentyl, hexyl, cyclopropyl, cyclobutyl, cyclopentyl, cyclohexyl, methylsilyl, dimethylsilyl, trimethylsilyl, ethylsilyl, diethylsilyl, triethylsilyl, propylsilyl, dipropylsilyl, tripropylsilyl, butylsilyl, dibutylsilyl, tributylsilyl, trifluoromethyl, phenyl, biphenyl, terphenyl, naphthyl, fluorenyl, benzyl, phenylethyl, phenylpropyl, phenylsilyl, phenyldimethysilyl, diphenylmethylsilyl, triphenylsilyl, methylphenyl, dimethylphenyl, trimethylphenyl, ethylphenyl, diethylphenyl, triethylphenyl, propylphenyl, dipropylphenyl, tripropylphenyl, methoxy, ethoxy, propoxy, butoxy, pentoxy, hexyloxy, methylsiloxy, dimethylsiloxy, trimethylsiloxy, ethylsiloxy, diethylsiloxy, triethylsiloxy, phenoxy, naphthoxy, methylphenoxy, dimethylphenoxy, trimethylphenoxy, ethylphenoxy, diethylphenoxy, triethylphenoxy, propylphenoxy, dipropylphenoxy, tripropylphenoxy, fluorine, chlorine, bromine, iodine, dimethylamino, diethylamino, dipropylamino, dibutylamino, diphenylamino, and dibenzylamino.

17. The multinuclear catalyst for olefin polymerization as claimed in claim 2, wherein $Cp^1$ and $Cp^2$ are cyclophentadienyl, methylcyclopentadienyl, dimethylcyclopentadienyl, trimethylcyclopentadienyl, tetramethylcyclopentadienyl, ethylcyclopentadienyl, diethylcyclopentadienyl, triethylcyclopentadienyl, n-propylcyclopentadienyl, iso-propylcyclopentadienyl, n-butylcyclopentadienyl, iso-butylcyclopentadienyl, tert-butylcyclopentadienyl, indenyl, methylindenyl, dimethylindenyl, trimethylindenyl, ethylindenyl, diethylindenyl, or triethylindenyl.

18. The multinuclear catalyst for olefin polymerization as claimed in claim 2, wherein the arylene group of $B^1$ is with or without heteroatom, and selected from biphenylene, terphenylene, naphthylene, binaphthylene, fluorenylene, anthracylene, pyridylene, biphenylene, terpyridylene, quinolylene, pyridazylene, pyrimidylene, pyrazylene, or quinoxalylene.

19. A multinuclear catalyst for olefin polymerization comprising:
(A) a transition metal compound represented by the formula 1:

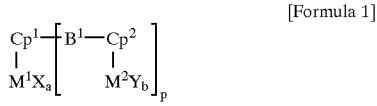
[Formula 1]

wherein $M^1$ and $M^2$ are the same or different and each represents an element in the groups III to X of the Periodic Table of the Elements; $Cp^1$ and $Cp^2$ are the same or different and each represents a ligand having an unsubstituted or substituted cyclopentadienyl structure, the substituted cyclopentadienyl structure having at least one substituent selected from the group consisting of a $C_1$–$C_{20}$ alkyl group, a $C_3$–$C_{20}$ cycloalkyl group, a $C_1$–$C_{20}$ alkylsilyl group, a $C_1$–$C_{20}$ haloalkyl group, a $C_6$–$C_{20}$ aryl group, a $C_7$–$C_{20}$ arylalkyl group, a $C_8$–$C_{20}$ arylsilyl group, a $C_7$–$C_{20}$ alkylaryl group, a $C_1$–$C_{20}$ alkoxy group, a $C_1$–$C_{20}$ alkylsiloxy group, a $C_8$–$C_{20}$ aryloxy group, a halogen atom and an amino group; and $B^1$ represents
a $C_{12}$–$C_{40}$ arylene group or an arylene group represented by the formula 2:

[Formula 2]

wherein Ary represents a $C_6$–$C_{20}$ arylene group directly bonded to $Cp^1$ and $Cp^2$, $B^{1'}$ represents a $C_1$–$C_{20}$ alkylene group, a $C_3$–$C_{20}$ cycloalkylene group, a $C_1$–$C_{20}$ alkylsilylene group, a $C_1$–$C_{20}$ haloalkylene group, a $C_7$–$C_{20}$ arylalkylene group or a $C_6$–$C_{20}$ arylsilylene group; and q is an integer from 0 to 5;

X and Y are the same or different and each represents $Cp^1$ or $Cp^2$, a $C_1$–$C_{20}$ alkyl group, a $C_3$–$C_{20}$ cycloalkyl group, a $C_1$–$C_{20}$ alkylsilyl group, a $C_1$–$C_{20}$ haloalkyl group, a $C_6$–$C_{20}$ aryl group, a $C_7$–$C_{20}$ arylalkyl group, a $C_6$–$C_{20}$ arylsilyl group, a $C_6$–$C_{20}$ alkylaryl group, a $C_1$–$C_{20}$ alkoxy group, a $C_1$–$C_{20}$ alkylsiloxy group, a $C_6$–$C_{20}$ aryloxy group, a halogen atom, an amino group or a tetrahydroborate group; a and b are an integer from 1 to 5 determined by the oxidation number of the central metal; and p is an integer from 1 to 3; and (B) an aluminoxane compound represented by the formula 9, an organoaluminum compound represented by the formula 10, or bulky compound represented by the formula 11 that is reactive to the transition metal compound to impart a catalytic activity to the transition metal compound:

[Formula 9]

wherein $R^1$ represents a $C_1$–$C_{10}$ alkyl group; and n is an integer from 2 to 70;

[Formula 10]

wherein $R^2$, $R^3$, $R^4$ are the same or different and each represents a $C_1$–$C_{10}$ alkyl group, a $C_1$–$C_{10}$ alkoxy group or a halide group, at least one of $R^2$, $R^3$, $R^4$ is an alkyl group; and

[C][D]
[Formula 11]

wherein C represents a protonated cation of a Lewis base, or an oxidative metallic or non-metallic compound; and D is a compound of an element found in groups V to XV of Periodic Table of the Elements and an organic substance, wherein $B^{1'}$ is methylene, dimethylmethylene, diethylmethylene, diphenylmethylene, ethylene, methylethylene, dimethylethylene, trimethylethylene, tetramethylethylene, tetraethylethylene, tetraphenylethylene, propylene, butylene, dimethylsilylene, diethylsilylene, diphenylsilylene, cyclohexylene or tetrafluoroethylene.

20. A supported multinuclear catalyst for olefin polymerization comprising:
(A) a transition metal compound represented by the formula 1:

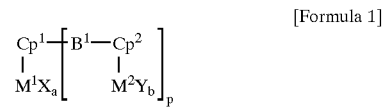
[Formula 1]

wherein $M^1$ and $M^2$ are the same or different and each represents an element in the groups III to X of the Periodic Table of the Elements; $Cp^1$ and $Cp^2$ are the same or different and each represents a ligand having an unsubstituted or substituted cyclopentadienyl structure, the substituted cyclopentadienyl structure having at least one substituent selected from the group consisting of a $C_1$–$C_{20}$ alkyl group, a $C_3$–$C_{20}$ cycloalkyl group, a $C_1$–$C_{20}$ alkylsilyl group, a $C_1$–$C_{20}$ haloalkyl group, a $C_6$–$C_{20}$ aryl group, a $C_7$–$C_{20}$ arylalkyl group, a $C_6$–$C_{20}$ arylsilyl group, a $C_7$–$C_{20}$ alkylaryl group, a $C_1$–$C_{20}$ alkoxy group, a $C_1$–$C_{20}$ alkylsiloxy group, a $C_6$–$C_{20}$ aryloxy group, a halogen atom and an amino group; and $B^1$ represents
a $C_{12}$–$C_{40}$ arylene group or an arylene group represented by the formula 2:

[Formula 2]

wherein Ary represents a $C_6$–$C_{20}$ arylene group directly bonded to $Cp^1$ and $Cp^2$; $B^{1'}$ represents a $C_1$–$C_{20}$ alkylene group, a $C_3$–$C_{20}$ cycloalkylene group, a $C_1$–$C_{20}$ alkylsilylene group, a $C_1$–$C_{20}$ haloalkylene group, a $C_7$–$C_{20}$ arylalkylene group or a $C_6$–$C_{20}$ arylsilylene group; and q is an integer from 0 to 5;

X and Y are the same or different and each represents $Cp^1$ or $Cp^2$, a $C_1$–$C_{20}$ alkyl group, a $C_3$–$C_{20}$ cycloalkyl group, a $C_1$–$C_{20}$ alkylsilyl group, a $C_1$–$C_{20}$ haloalkyl group, a $C_6$–$C_{20}$ aryl group, a $C_7$–$C_{20}$ arylalkyl group, a $C_6$–$C_{20}$ arylsilyl group, a $C_6$–$C_{20}$ alkylaryl group, a $C_1$–$C_{20}$ alkoxy group, a $C_1$–$C_{20}$ alkylsiloxy group, a $C_6$–$C_{20}$ aryloxy group, a halogen atom, an amino group or a tetrahydroborate group; a and b are an integer from 1 to 5 determined by the oxidation number of the central metal; and p is an integer from 1 to 3; and (B) an aluminoxane compound represented by the formula 9, an organoaluminum compound represented by the formula 10, or bulky compound represented by the formula 11 that is reactive to the transition metal compound to impart a catalytic activity to the transition metal compound:

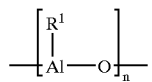

[Formula 9]

wherein $R^1$ represents a $C_1$–$C_{10}$ alkyl group; and n is an integer from 2 to 70;

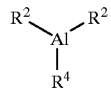

[Formula 10]

wherein $R^2$, $R^3$, $R^4$ are the same or different and each represents a $C_1$–$C_{10}$ alkyl group, a $C_1$–$C_{10}$ alkoxy group or a halide group, at least one of $R^2$, $R^3$, $R^4$ is an alkyl group;

[C][D]   [Formula 11]

wherein C represents a protonated cation of a Lewis base, or an oxidative metallic or non-metallic compound; and D is a compound of an element found in groups V to XV of Periodic Table of the Elements and an organic substance; and an organic or inorganic support,
wherein the organic support is starch, cyclodextrine, or synthetic polymer.

* * * * *